United States Patent
McNew

(10) Patent No.: US 7,141,028 B2
(45) Date of Patent: Nov. 28, 2006

(54) APPARATUS, SYSTEM, AND METHOD FOR CREATING AN INDIVIDUALLY, BALANCEABLE ENVIRONMENT OF SOUND AND LIGHT

(76) Inventor: Barry McNew, 34 N. Alamos Dr., Cottonwood, AZ (US) 86326

( * ) Notice: Subject to any disclaimer, the term of this patent is extended or adjusted under 35 U.S.C. 154(b) by 0 days.

(21) Appl. No.: 11/013,778

(22) Filed: Dec. 16, 2004

(65) Prior Publication Data

US 2006/0030907 A1 Feb. 9, 2006

Related U.S. Application Data

(63) Continuation-in-part of application No. 10/408,537, filed on Apr. 7, 2003, now Pat. No. 7,108,654, which is a continuation of application No. 09/359,819, filed on Jul. 22, 1999, now Pat. No. 6,544,165.

(60) Provisional application No. 60/530,732, filed on Dec. 17, 2003.

(51) Int. Cl.
*A61H 1/00* (2006.01)
*A61M 21/00* (2006.01)

(52) U.S. Cl. .............................. 601/15; 601/47; 600/28

(58) Field of Classification Search ................. 601/15, 601/18, 46, 47, 49, 56, 57; 600/26–28, 300; 128/897–898, 905
See application file for complete search history.

(56) References Cited

U.S. PATENT DOCUMENTS

| 3,085,568 A | * | 4/1963 | Whitesell ...................... 601/55 |
| 6,544,165 B1 | * | 4/2003 | McNew ........................ 600/27 |
| 6,656,137 B1 | * | 12/2003 | Tyldsley et al. ............... 601/15 |
| 6,702,767 B1 | * | 3/2004 | Douglas et al. ............... 601/15 |

* cited by examiner

*Primary Examiner*—Quang D. Thanh
(74) *Attorney, Agent, or Firm*—Kunzler & Associates

(57) ABSTRACT

An system, apparatus, and method are disclosed for therapeutic light and sound, comprising the steps of exposing a user to spectral light and laterally directed sound and adjusting the manner of exposure sufficient to elicit a desired autonomic nervous response.

21 Claims, 14 Drawing Sheets

LEGEND

902 — Large Transducer
904 — Medium Transducer
906 — Small Transducer

APPARATUS, SYSTEM, AND METHOD FOR CREATING AN INDIVIDUALLY, BALANCEABLE ENVIRONMENT OF SOUND AND LIGHT

CROSS-REFERENCES TO RELATED APPLICATIONS

This application claims the benefit of Provisional Application No. 60/530,732, entitled "METHOD AND APPARATUS FOR CREATING AN INDIVIDUALLY BALANCEABLE ENVIRONMENT OF SOUND AND LIGHT" filed on Dec. 17, 2003, and is a continuation-in-part of application Ser. No. 10/408,537, entitled "METHOD AND APPARATUS FOR APPLYING FREQUENCY VIBRATIONS THERAPEUTICALLY" filed on Apr. 7, 2003 now U.S. Pat. No. 7,108,654, which is a continuation of application Ser. No. 09/359,819, entitled "METHOD AND APPARATUS FOR APPLYING FREQUENCY VIBRATIONS THERAPEUTICALLY" and filed on Jul. 22, 1999, now U.S. Pat. No. 6,544,165. All are incorporated herein by reference.

BACKGROUND OF THE INVENTION

1. Field of the Invention

This invention relates to a method and apparatus for creating an individually balanced environment of sound and light.

2. Description of the Related Art

Certain benefits of utilizing light, sound, color, and vibration are known. Medical evidence indicates that the health of people may be affected by exposure to light. The scientific investigation and therapeutic use of light in medicine has its origins well over a century ago in the works of Edwin D. Babbitt, M. D. (*The Principles of Light and Color*, 1873) and Seth Pancoast, M. D. (*Blue and Red Light or Light and Its Rays as Medicine,* 1877).

The "Spectro-Chrome" therapy, developed by scientist/inventor Dinshah P. Ghadiali and utilized in the U.S. from roughly 1920–1950, was used successfully by Dr. Kate W. Baldwin at the Philadelphia Women's Hospital to aid in the healthy regeneration of skin tissue in the case of severe and extensive burns on the body. The Spectro-Chrome therapy involved repeatedly exposing certain areas of the body to certain colors of light for a fixed duration of time. Colored light therapy research was furthered in the 1940's by Russian scientist S. V. Krakov, who was the first to examine its effects on the autonomic nervous system. Chromotherapy, the therapeutic use of light of particular colors, is believed to interact with the body via the skin and the eyes which may function as receptors.

Intensity of light and its overall spectral components are also known to be important. Utilization of sunlight as a cure for jaundice was discovered by accident in 1956 by Sister Ward of Rochford General Hospital in England. More recent studies have examined the role of sunlight and full-spectrum lighting to address Seasonal Affective Disorder and a host of other health disorders including bulimia, delayed sleep phase syndrome, and regulation of menstrual cycles.

It is also known that sound plays a substantial role in changes of pulse frequency, blood pressure, blood circulation, muscle relaxation, perspiration, and oxygen consumption of a person. Sound therapy is well documented medically to have a profound effect on human health. Rhythm, pitch, frequency (tone), intensity, resonances, harmonics, and vibration all affect the body. The therapeutic use of sound (e.g., in the form of music) has ancient roots, but Burton Goldberg in *Alternative Medicine*, cites a medical investigation of the effect of sound on the human body as early as 1896. Medicine's recent understanding of the interconnectedness of the sub-cellular and intracellular tissue-tensegrity matrix of the body, often referred to as the living matrix, prove the effects of sound on the body to be profound. Sound is composed of pressure waves which are not only perceived by the auditory system of the body, but are felt as vibrations as well. Auditory signals are understood to be carried to the vagus nerve in the body via, for example, the eighth and tenth cranial nerves. The vagus nerve extends to all of the visceral organs of the body and, in addition to regulating breathing, heart rate and speech, also affects the immune system.

Cymatic therapy, developed by Sir Peter Guy Manners, M. D., applies audible sound to the skin to stimulate natural regulatory and immunological systems, and to produce a near-optimum metabolic state for a particular cell or organ. Dr. Manners is said to have identified the healthy vibrational resonance frequency of tissues and organs in the body. Computerized cymatic therapy allegedly transmits the appropriate audio resonance frequencies needed to reestablish healthy resonance in unhealthy tissues. According to Goldberg, cymatic therapy has been in use in the U.S. since the 1960's and has no known side affects (although it cannot be used on patients with pacemakers). An important point about cymatic therapy is that it does not purport to heal but, rather, effectively places the body in such a state that its own natural ability to heal is enhanced.

Sound can also be utilized to affect brainwave states, as extensively investigated and documented by Robert Monroe and the Monroe Institute. The effects of binaural beats, the brain's integration of two coherent sound waves that are very close in frequency to generate the sensation of a third sound from the brainstem's superior olivary nucleus, are neurologically conveyed to shift brainwaves. The Monroe Institute's Hemi-Sync™ audio technology embeds binaural beat patterns in music to induce relaxed or other altered consciousness states. Integrative medicine champion Dr. Andrew Weil has recently released a book/CD entitled, *Sound Body, Sound Mind: Music for Healing*, which also utilizes binaural beats in music to induce relaxation, shifted consciousness/brainwave states, and restorative healing. This new field of psychoacoustics adds an additional dimension to the examination of any healing technology that utilizes sound therapeutically.

Further, it is well known that the different parts of the human brain are known to relate to different parts of the body; for example, the two hemispheres of the brain are known to relate to different sides of the body.

The role of the autonomic nervous system has also been gaining significant amounts of attention. The autonomic nervous system (ANS) is the portion of the nervous system that controls (subconsciously) the function of the different organs and systems of the body. For instance, the ANS regulates heartbeat rate, body temperature, blood pressure, breathing, and bowel and bladder tone, among other variables. It is "autonomic" because our conscious mind does not govern its performance; rather, it works below the level of awareness. An important characteristic of the ANS is the rapidity and intensity of the onset of its action and its dissipation. Centers located in the central nervous system (e.g., brain stem, hypothalamus, and thalamus) and in the spinal cord activate the ANS. These centers also receive input from the limbic system and other higher brain areas. The ANS is thus considered to be the interface between the mind and body functions. These connections enable the ANS to be the main component of the stress response system in charge of fight-or-flight reactions.

The ANS also works closely with the endocrine system (e.g., the hormonal system), particularly the hypothalamic-pituitary-adrenal axis. Another endocrine axis closely related to the ANS involves growth hormone secretion.

The peripheral autonomic system is discussed in terms of two branches: the sympathetic branch and the parasympathetic branch. These two branches have antagonistic effects on most bodily functions, and their proper balance is believed to preserve equilibrium (as well as health or wellness) in the body. Sympathetic activation prepares the whole body for fight-or-flight in response to stress or emergencies. In contrast, parasympathetic activation favors digestive functions and sleep.

The sympathetic autonomic branch extends from the brain stem to the spinal cord and features quite extensive sympathetic nerve tissue in the neck and pelvic areas. From the spinal cord, the sympathetic nervous system is connected to the internal organs and to the extremities. At the skin level, sympathetic activity induces, for example, clammy hands, mottled skin, and piloerection (i.e., goose flesh).

The action of the two branches of the ANS is mediated by neurotransmitters. Adrenaline, which is also known as norepinephrine, is the predominant sympathetic neurotransmitter, whereas acetylcoline acts in the parasympathetic system.

Until recently, the action of the extremely dynamic ANS has been difficult to assess by clinical techniques. Changes in breathing pattern, mental stress, or even posture alter immediately and completely the sympathetic/parasympathetic balance. However, the introduction of a new and very powerful cybernetic technique known as heart rate variability analysis ("HRV") has permitted nearly instantaneous data collection from individuals without any bodily intrusions or invasions. A particularly useful HRV device is an FDA approved product known as the ANX 3.0 manufactured by ANSAR, Inc., 240 South Eighth Street, Philadelphia, Pa. 19107. The variations in heart rate are one of the main parameters tracked in HRV measurements. In particular, the HRV technique is based on the fact that the heart rate is not uniform but varies continuously from beat to beat by a few milliseconds. The periodic components of this endless heart rate variation are dictated by the antagonistic impulses that the sympathetic and parasympathetic branches have on the heart. Cybernetic recording of this constant variability is able to estimate both sympathetic and parasympathetic activity. The elegance of the HRV technique resides primarily in the fact that all measurements are derived from electrocardiograms, so individuals are subjected to almost no discomfort at all during the collection of data.

In particular, HRV measurements are made by connecting an individual to a series of externally applied electrodes, connecting a finger to a pulse oximetry detector and then subjecting an individual to a series of regular breathing, deep breathing, standing, and Valsalva exercises and monitoring the subsequent physical response of the body (e.g., how the sympathetic and parasympathetic components of the ANS together function). In general, a person in a healthy state is perceived to have nearly balanced sympathetic and parasympathetic activity of the autonomic nervous system.

It is further known that natural narcotic-like molecules named endocannabinoids are released by the brain. (R. Nicoll and B. Alger, The Brain's Own Marijuana, *Scientific American*, December 2004. p. 68.) These molecules participate in regulating hunger, anxiety, pain, and other reactions. Endocannabinoids facilitate the process of retrograde signaling, or depolarization-induced suppression of inhibition. ("DSI"). DSI enhances a form of learning called long-term potentiation, in which information is stored through the strengthening of synapses. In effect, DSI allows individual neurons to briefly disconnect from the neural network and encode information.

Recent studies have linked DSI to anxiety recovery. Rodents lacking endocannabiniod receptors, like normal rodents, can learn an anxiety response to, for example, a bell initially accompanied by an electric shock. Unlike normal rodents, however, the receptor-deficient rodents never lose the anxiety response upon repeated exposure to the bell without the electric shock. Such research suggests the importance of endocannabinoids in recovery from such conditions as post-traumatic stress syndrome.

Various stimuli foster the release of endocannabinoids, which appear to be more abundant in some individuals than others. Recent research suggests that cognition, learning, memory, and anxiety recovery would be enhanced by an environment that encourages the release of endocannabinoids.

Notwithstanding the interrelated and delicately tuned effect of light and sound on an individual user, previous practice has relied either upon the judgment of a practitioner or accepted knowledge as to what frequencies of sound and/or light should be applied to create a benefit. Yet, from the foregoing discussion, it should be apparent that a need exists for an apparatus, system, and method provides an environment of sound and light customized to an individual user.

SUMMARY OF THE INVENTION

The present invention has been developed in response to the present state of the art, and in particular, in response to the problems and needs in the art that have not yet been fully solved by currently available light and sound environments. Accordingly, the present invention has been developed to provide a system, apparatus, and method for creating an individually balanced environment of light and sound.

The disclosed system, apparatus, and method provide a resonant enclosure containing an environment of music and light which can be balanced individually with respect to a living being substantially contained within said enclosure. In one embodiment the resonant enclosure may be tuned to resonate in the range of a specific musical tone, for example C flat minor. The depicted embodiments achieve the balanced environment by using acoustic vibrations, also known as sound, directed to, for example, the right and left sides of the individual's body. Certain forms of the enclosure could also act as a sound reflector to direct acoustic vibrations to the skin and ears of the individual.

Various embodiments provide a substantially dark space (e.g., created by an enclosure) which includes at least one light source for controlling light emitted on to the individual. Moreover, such light may comprise white light or is separated into a spectrum of colors.

The environment of music and light may be balanced individually with respect to a user substantially contained within the resonant enclosure. The environment of sound and light created therein produces physiological responses in the individual which may specifically guide either an operator or an automated control system to provide those combinations of frequencies of sound and light needed to cause beneficial autonomic responses in the individual. Hence, via this feedback process, the individual user effectively defines the specific sound and light environment appropriate for the user's exposure. In other words, the frequency, intensity, and duration of sound and light applied to the user is determined by the user's body. The present invention tunes and adjusts the sound and light environment based on the user's response.

A system is disclosed for creating an individually balanceable environment of sound and light, the system comprising a signal generator, at least one selectively energized transducer, at least one selectively energized light source, and one or more controllers for adjusting the light source and the acoustical vibrations of the transducer sufficient to elicit a desired autonomic nervous response.

In another embodiment of the system the transducer may be configured to selectively direct sound waves to a region of the user including the upper, center, and lower sections of the right and left side. In another embodiment of the invention one transducer or any of a plurality of transducers may be separately controlled by an actuating switch, enabling sound to be directed to a specific region of the user's body and a light switch may be configured to control at least the intensity of the light source. The system may further comprise collections of selected musical compositions.

The system may further include at least one attenuating barrier located between transducers arranged on opposite sides of the longitudinal centerline. Additionally, the enclosure module may be tuned to a musical tone.

In a further embodiment a monitor may be configured to monitor the response of the user to the applied light and sound. This may be done through direct observation of, for example, the user's eye movement. The monitor may also monitor the autonomic nervous system of the user. The monitor may be configured to measure changes in the user's heart beat through, for example, heart rate variation ["HRV"] technique An apparatus for therapeutic light and sound is also presented. In one embodiment the apparatus comprises a support structure comprising a longitudinal centerline and a top side for supporting a user, a pair of speakers arranged on the support structure for transmitting acoustic vibrations selectively to a right side and a left side of the user, at least one attenuating barrier located between the pair of speakers arranged on opposite sides of the longitudinal centerline, at least one light source comprising visible light and one or more controllers configured to adjust acoustical vibrations produced by the speakers and intensity of the light source such that the acoustic vibrations and the light source are coordinated to therapeutically stimulate the user; and a monitor configured to monitor at least one of the user's autonomic nervous system and the user's response to the applied light and sound.

In a further embodiment apparatus further comprising an enclosure module surrounding the user. The enclosure may additionally comprise a resonant cavity configured to transmute applied acoustical vibrations to a lower frequency. The enclosure module may also be tuned to a musical tone of a C flat minor chord.

The speakers may be configured to operate between about 10 Hz and about 25,000 Hz and the at least one light source may be configured to deliver light to the user with a wavelength in a range from about 400 nanometers to about 800 nanometers. One or more reflective surfaces may be positioned around the light source as separate surfaces or in a frame configuration.

An embodiment of a method for therapeutic light and sound, is also presented. The disclosed method comprises exposing a user to spectral light and directed sound and adjusting the manner of exposure sufficient to elicit a desired autonomic nervous response. In a further embodiment the method comprises transmitting acoustical vibrations specifically to a specific region of the user's body, for example the upper, middle, and lower region of the user's right and left side. The method may further comprise the step enclosing the user in a support module and the step and the step of tuning the support module to a specific musical tone. Additionally, at least one eye of the user may be enclosed in an substantially dark space coupled to a source of visible light.

A further embodiment may include the step of generating acoustical vibrations using a sound generator and the step of calibrating the sound frequency to, for example, between about 10 Hz and about 30,000 Hz, or to the sympathetic resonance of specific body tissues. A further step may comprise separately controlling the sound generator and at least one selectively energized light source using a controller.

The method may also include the step of monitoring one or both of the user's response to the applied light and sound and the user's autonomic nervous system by means of an operator, a controller, or a monitor. In a further step of either or both of the light and sound frequency may be adjusted according to the monitoring feedback. The adjustment may be performed manually or automatically. In some cases the method may include the step of monitoring the state of the user's autonomic nervous system either or both of before and after treatment. Adjustments in the frequency and intensity of the light and sound may be calibrated to the state of the autonomic nervous system of the user.

The operator, controller, and monitor may be embodied in a variety of forms, for example, an individual, an optical device such as a digital camera, a specifically designed device, or a software program running on a computer.

A means for delivering therapeutic light and sound to a user is also presented. In the disclosed embodiment the means may comprise a user support means, a sound generating means, at least one means for selectively directing sound to a specific region of the user's body, an enclosure means coupled to at least one selectively energized light means, a means for controlling the frequency of the sound, a means for controlling at least the intensity of the light, a means for communicating with a user, a means for monitoring the response of the user; and a means for feedback adjustment of at least one of the intensity and frequency of the light and sound.

In the various embodiments certain combinations of sound and light are applied to a human or animal user within certain predetermined ranges, and adjusted based upon unique physiological responses (discussed in greater detail below) from the user. In the case of humans, the combinations of sound and light within the enclosure are balanced in such a manner (also as later described herein) as to result in near balance of the parasympathetic and sympathetic elements of the nervous system of the being, as can be demonstrated in the case of humans by HRV monitor readings before and after exposure of the human being to the balanced environment of sound and light of the present invention.

Humans within this balanced environment frequently report feelings of destressing, wellness, inspiration, and creativity. Sometimes they also report enhanced perceptions, such as lucid remote viewing, and occasionally perceptions of out-of-body experiences. It is frequently observed that toxins, such as heavy metals and anesthetics, begin to be spontaneously ejected from the individual's body exposed to this environment, as observed by concurrent vapor odors and subsequent urinalysis. A common aftereffect of the exposure of an individual to the balanced environment of music and light of the present invention appears to be restoration of an innate ability of the individual to heal the self, apparently regardless of the nature of an affliction.

Specifically, humans exposed to the balanced environment of sound and light of the present invention have reported subsequent spontaneous healings of drug addiction, autism, multiple sclerosis, cancer, Type II diabetes, back pain, overweight, fibromyalgia, hypoglycemia, amnesia, scleroderma, eczema, migraines, seizures, allergies and a host of other diseases, all of which were previously medically diagnosed. Two dogs individually exposed to the balanced environment of sound and light of the present invention were afterward observed to spontaneously recover from an enlarged heart and cancerous tumors, respectively, both of which were previously medically diagnosed.

It is presently believed by many in the medical community that cell repair for humans occurs in the REM (Rapid Eye Movement) sleep state, which corresponds to a human brainwave state in the frequency range of 8 Hz. Further, it is known that in the REM state release of neurotransmitters such as norepinephrine, serotonin and histamine does not occur, but rather only occurs in higher frequency brainwave states such as non-REM sleep and waking states. Since release of such neurotransmitters is required for enabling body movement and awareness of one's environment, cell repair in humans is typically only occurring a small percentage of the time. Elevated human consciousness states, such as those involved with meditation and remote viewing, have been observed by several researchers to correspond to lower frequency brainwave activity at and below 8 Hz. Meditative states are believed by many to provide destressing and healing benefits to the meditator. During such elevated consciousness states, however, conscious awareness of the environment is usually reduced.

It has been observed that, under the conditions of the balanced environment of sound and light of the present invention, humans tend to exhibit brainwave states encompassing frequencies at or below 8 Hz, while at the same time being capable of remaining fully conscious. Furthermore, such higher consciousness levels evidenced by such low frequency brainwave components tend to be sustained in the individual in fully conscious states thereafter as an aftereffect of their exposure to the balanced environment of sound and light of the present invention. While not wishing to be bound by any particular theory, it is believed that healing aftereffects reported by individuals exposed to the balanced environment of sound and light of the present invention are due to continuing cell repair and neurogenesis capability enabled in the individual by such higher consciousness states being sustained throughout both their waking and sleeping conditions.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

A number of the functional units described in this specification have been labeled as modules, in order to more particularly emphasize their implementation independence. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

In accordance with this invention, a system, apparatus, and methods for creating an individually balanced environment of sound and light are disclosed. Moreover, while environments of both sound and light have previously been employed for providing various beneficial effects upon an individual, the available technology has relied either upon the judgment of a practitioner or accepted knowledge as to what frequencies of sound and/or light should be applied to create a benefit. The existing art has lacked the means receive quantitative guidance from the unique responses of an individual user to applied sound and light.

Sound and light, however, do produce physiological responses in the individual user, which could appropriately specifically guide either an operator or a control system to provide those combinations of frequencies of sound and light needed to create benefits to the user. Hence, via this feedback process of the present invention, it is the condition and responses of individual user that defines the specific sound and light environment for the user's exposure.

Figure 1:
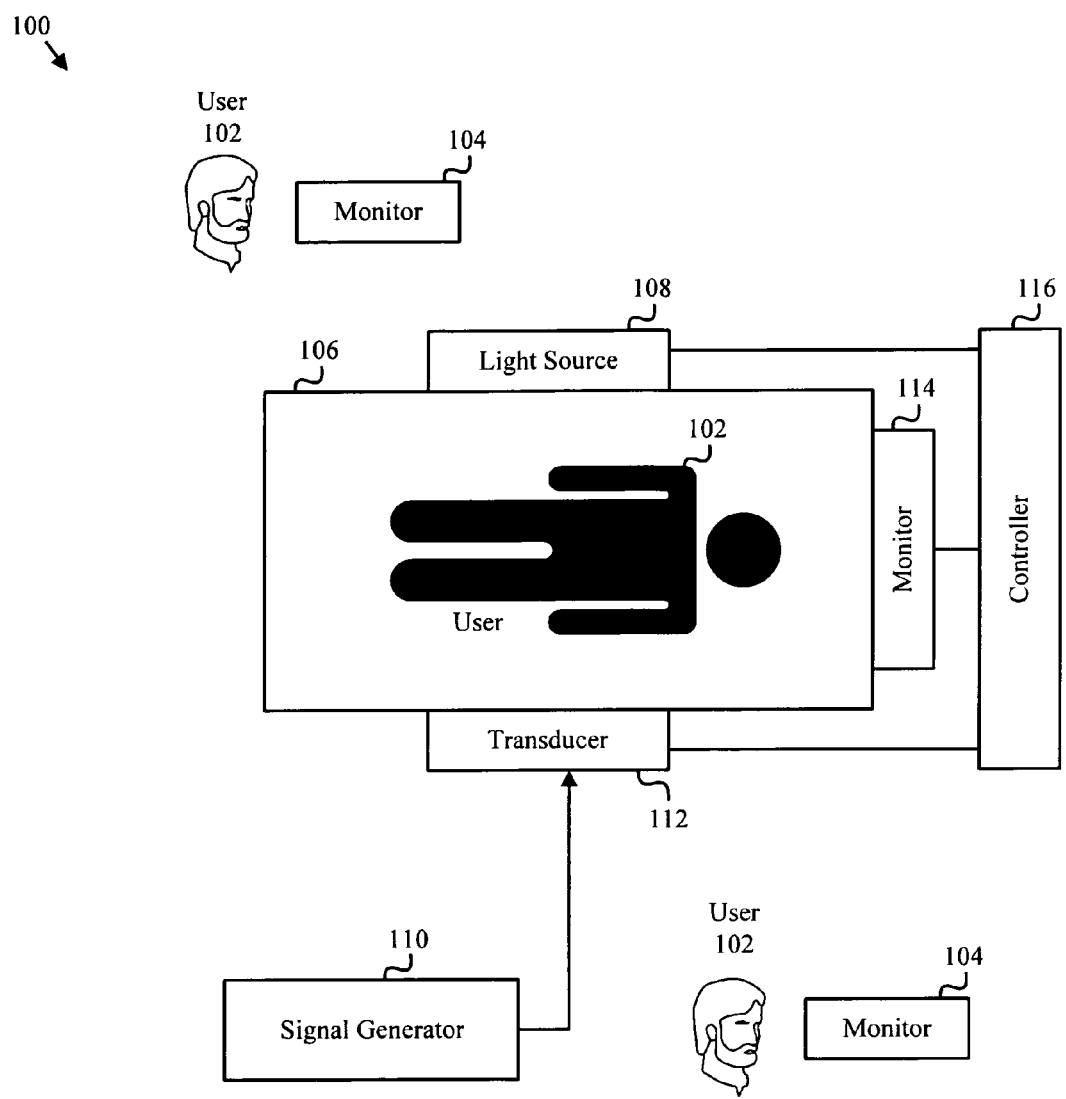
FIG. 1 is a schematic block diagram illustrating one embodiment of a system in accordance with the present invention.

FIG. 1 is a schematic block diagram illustrating one embodiment of a system 100 in accordance with the present invention. As depicted the system 100 comprises a user 102, an outside monitor 104, an enclosure module 106, a light source 108, a signal generator 110, a transducer 112, a treatment monitor 114, and a controller 116.

The outside monitor 104 may be located away from the enclosure module 106, and be used to monitor the autonomic nervous system of the user 102 prior and subsequent to treatment. In one embodiment the outside monitor 104 comprises an HRV monitor.

The treatment monitor 114 may be used in conjunction with treatment, to monitor the response of the user 102 to the applied light and sound. The controller 116 may adjust the light and sound according to feedback received from the treatment monitor 114. In one embodiment, the treatment monitor 114 and outside monitor 104 are combined in a single monitor that communicates light and sound feedback to the controller 116.

Typically the light source 108 is located in a position that would correspond to being above the eyes of a typical user reclining upon the bottom side of the enclosure with their spine more or less aligned with said longitudinal centerline, although in some cases the user will be positioned so that his or her feet are under the light source and their head is at the opposite end of the enclosure from the light source.

The system may also include a signal generator 110 for producing electromagnetic signals for actuating the transducers so as to produce appropriate sound. The signal generator 110 may be any sort of device that generates an electrical output which may be converted into appropriate acoustic vibrations. Examples of such types of signal generators include, but are not limited to, stereo systems, radio receivers, phonographs, compact disc players, tape recorders and players, cable box decoders, satellite signal capturing devices, televisions, video cassette recorders, Internet connecting devices, etc. In some cases sound and vibrational frequencies ("response vibrations") may be created within the device by nature of its design which are not directly accounted for by the transducer outputs; that is, harmonics and/or beat frequencies may result from configurational and/or resonance effects associated with the device and therefore also be present within.

In a further embodiment the electromagnetic signals may comprise music as depicted in table I. The musical selections may be organized into collections of sufficient length for a treatment session and the collections may be graded according to intensity. A user may typically begin with a lower intensity group and, according to condition and response, remain at that intensity or progress to groups of greater intensity. The highest intensity groups may be reserved for extreme situations.

TABLE 1

| Artist | Album Title | Publisher |
| --- | --- | --- |
| Aeoliah | Angel Love | Oreade Music |
| Chuck Wild | Liquid Mind III - Balance | Chuck Wild Records |
| Chuck Wild | Liquid Mind IV - Unity | Chuck Wild Records |
| Classical Relaxation | Mozart with Ocean Sounds | Direct Source Special Products, Inc. |
| Deuter | Reiki Hands of Light | New Earth Records |
| Dr. Jeffrey Thompson | Brainwave Suite Alpha | The Relaxation Company, Inc. |
| Dr. Jeffrey Thompson | Brainwave Suite Alpha-Theta | The Relaxation Company, Inc. |
| Dr. Jeffrey Thompson | Brainwave Suite Theta | The Relaxation Company, Inc. |
| Dr. Jeffrey Thompson | Brainwave Suite Delta | The Relaxation Company, Inc. |
| Gerald Jay Markie | Celestial Mozart for Relaxation | Astro Music |
| Erin Jacobsen | Feather on the Breath of God | Serenity Music |
| Inner Peace | Life! Beats | Metacom Music |
| Keiron | Stained Glass | Cathedral Whispers |
| Madwyn Goodall | Medicine Woman II - The Gift | New World Music Limited |
| Merlin's Magic | Angel Symphony of Love and Light | Inner Worlds Music |
| Merlin's Magic | Chakra Meditation Music | Inner Worlds Music |
| Merlin's Magic | The Heart of Reike | Inner Worlds Music |
| Michael Martin Murphy | Cowboy Songs | Steve Gibson Productions |
| Paul Michael Meredith | The Luxury of Love | |
| Peter Sterling | Heart and Soul | Harp Magic Music |
| Real Music | Land of Forever 2002 | Real Music Publishing |
| Real Music | Tranquility - A Real Music Sampler | Real Music Publishing |
| Real Music | Wrapped in the Stillness - | Real Music Publishing |

TABLE 1-continued

| Artist | Album Title | Publisher |
| --- | --- | --- |
| A Pause in the Veil of Time | | |
| Real Music | Letting the World Go By | Real Music Publishing |
| Real Music | Chrysalis | Real Music Publishing |
| Robin Miler | Transcendence | R. M. Productions |
| Steven Halpern Music | Spectrum Suite | Steven Halpern's Inner Peace |
| Steven Halpern Music | Gifts of the Angels | Steven Halpern's Inner Peace |

In many cases only part of a musical selection may be used, such as a single track, or even part of a track. Further, combinations of sounds or acoustic outputs from the music contained in Table 1 can be replicated, at least in part, by various acoustic generators (e.g., synthesizers, recording devices which are capable of screening out certain characteristics, etc.).

The physiologic responses occur at various combinations of sound (e.g., particular selections of music play at particular intensities through transducers or speakers) and light (e.g., particular frequencies, intensities and/or patterns) to which a user is exposed. For example, desirable music which can be used to at least partially create a balanced environment of sound and light includes, but is not limited to, the musical selections listed in Table 1. Specific musical selections are chosen and varied depending upon physiological response to a given selection. The musical selections, sound intensity, and light source settings appropriate to achieving balance in one individual are frequently not effective in achieving balance in another individual; hence these parameters are varied as necessary to achieve balance with each individual user. Appropriate musical selections, sound intensity, and light source settings seem to depend upon characteristics of the individual such as physical density, personal history, state of health, etc. As could be noted by analyzing the musical selections listed as examples in Table 1, the repertoire includes a wide range of frequencies and sound patterns.

Figure 2:
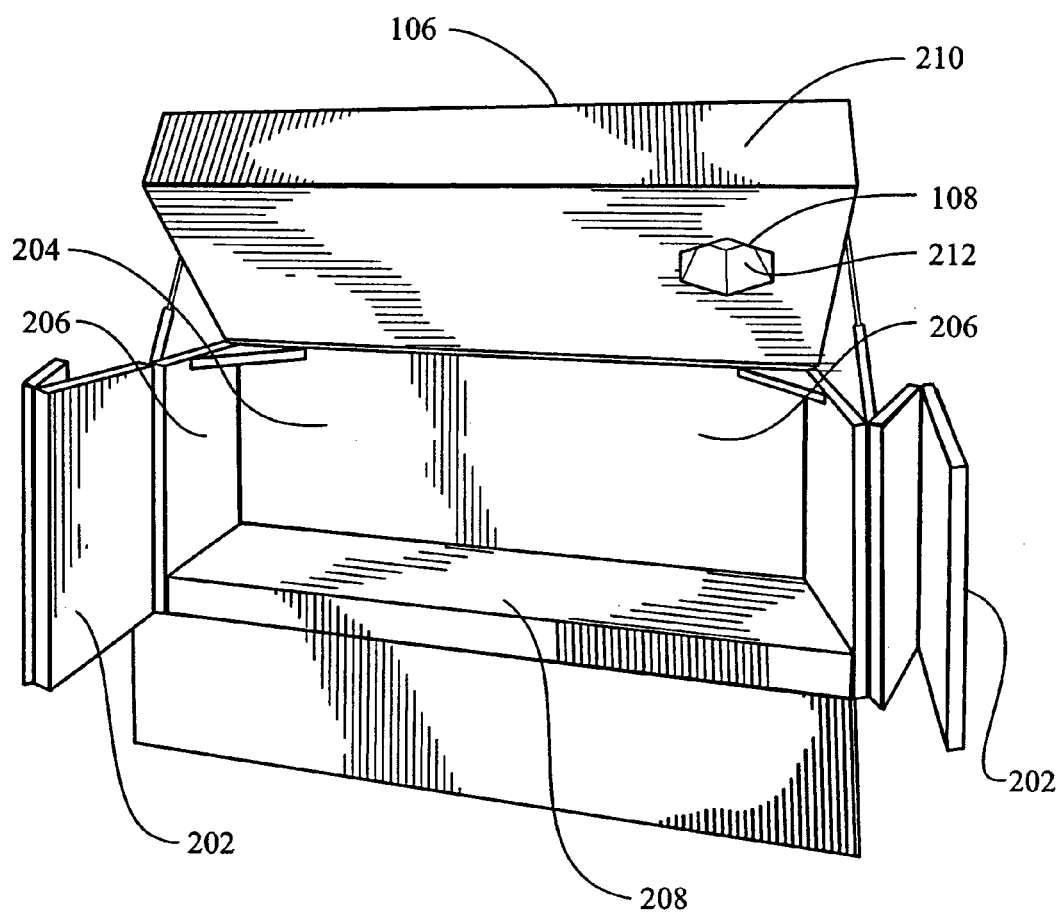
FIG. 2 is a photograph depicting one embodiment of an apparatus in accordance with the present invention.

FIG. 2 is a photograph depicting one embodiment of a enclosure module 106 in accordance with the present invention. As depicted, the enclosure module 106 comprises a folding front wall 202, a back wall 204, an end wall 206, a support structure 208, a top 210, a light source 108, and a reflective frame 212.

In the depicted embodiment the front wall 202 is divided into two sections, each of which is further divided into at least two sections and provided with an attachment means for bending or swinging on a vertical axis. Each of the two outside ends of the divided front wall 202 is movably attached at to the corresponding end wall 206. This allows the front wall 202 to close during use and to open allowing a user to enter and exit. The top 208 is movably attached to the back wall 204 for ease of use. A light source 108 is mounted on the underside of the top 208 and is surrounded by reflective frame 212. The support structure 208 supports the user.

The lower surface of the top 201 may be made of three-quarter inch thick fir plywood, covered on its lower surface by navy blue cotton sheet material, except for that portion where the light source 100 and its associated reflector 104 are exposed to the inside of the device. In a further embodiment the enclosure module may comprise a resonant cavity configured to resonate to specific acoustical wavelengths. The resonant cavity may further be tuned to a specific musical tone, for example c flat minor. In particular embodiments, the resonant cavity is configured to transmute accoustical vibrations to lower frequencies. While the sound produced directly by the transducers is typically 30 Hz and higher in frequencies, lower frequency response vibrations may be simultaneously created within the enclosure 106 in response to sound from the transducers by virtue of the design of the enclosure.

In the depicted embodiment an enclosure 106 is formed by a combination of the elements that together in a closed configuration form a substantially dark space such that the substantially dark space may be sufficiently large to accommodate a user. In one embodiment of the present invention, the enclosure 106 would provide an acoustic resonating layer attached to the inside vertical surfaces of the enclosure. Such layer may be constructed of three-eighths of an inch thick by two inch wide soft white pine tongue and groove segments installed vertically and covering the inside of the back wall 204, the front doors 202, and the end walls 206.

In another embodiment, the enclosure 106 could be covered outside with a light absorbing material rendering the enclosure substantially opaque to light transmission. In various embodiments the enclosure 106 may be of any size including of sufficient size to enclose the user. Examples of enclosures that can form a substantially dark space include cavities and rooms from which light can be substantially excluded. However, it must be remembered that the enclosure 106 is designed to be a tuned enclosure, preferably designed to resonate in the range of the musical tone c flat minor, and therefore should be of dimensions and materials consistent with that characteristic.

In the depicted embodiment the front wall 202 of the enclosure 106 is segmented into two two-part doors 202, each with a pivoting means toward the center, so that the wall can be folded open to the sides thereby forming a convenient access port through which the user can may enter and exit the enclosure 106. Other access ports may be created in the enclosure 106, for example through the support 208 if there is room, or through ends 206, or through top 201, etc. In further embodiments, a communication system may be provided so that the user and a person outside the system may communicate.

Figure 3:
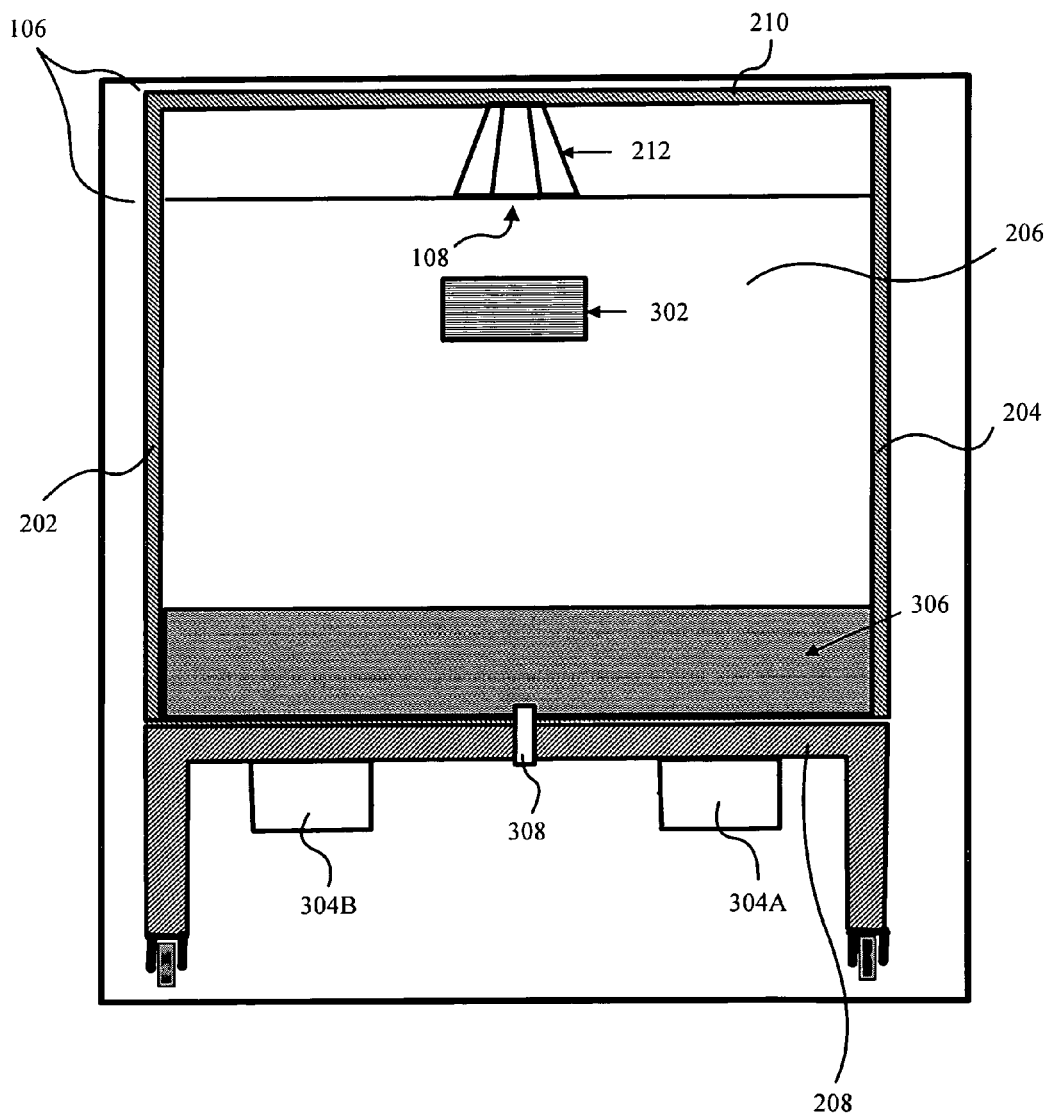
FIG. 3 is a schematic line drawing depicting a cross-sectional view of an apparatus for creating an individually balanceable environment of sound and light in accordance with the present invention.

FIG. 3 is a non-limiting schematic line drawing illustrating a cut-away end view of one embodiment of an apparatus 300 for creating an individually balanced environment of light and sound according to the present invention. As depicted, the apparatus 300 comprises the enclosure module 106, the front wall 202, the back wall 204, the end walls 206, the support structure 208, the top 210, the light source 108, the reflective frame 212, a vent 302, transducers 304 a mat 306, and a longitudinal centerline 308.

The enclosure module 106 of the apparatus 300 may include a support structure 208 having a longitudinal centerline, a top side, and a bottom side for supporting a user; at least two transducers 304 arranged on opposite sides of the longitudinal centerline for producing acoustical vibrations substantially directed to the right side and left side of the user, respectively, and at least one variably energized light source 108 coupled to the otherwise substantially dark space for transmitting light to the user. The mat 306 may placed on the top side of the support structure 208 for cushioning the user and transmitting acoustical waves to the right side and left side of the user's body. Sound generators or transducers 304 may be arranged for separately transmitting acoustic vibrations to the right side and left side of the user.

The support 208 should be large enough to support the user and of sufficient strength to remain substantially rigid when subjected to the user's weight. Examples of materials that can be used for the support include, but are not limited to, wood, sound board, plywood, particle board, composite insulation board, plastic, glass, Plexiglas, fiberglass, metal, stone, marble, etc. Preferably the support material would be made of three-quarter inch thick fir plywood and would provide a sound insulating material such as polyurethane foam that could be attached to the upper surface of the support material. Such insulating material serves as a sound equalizer transmitting sound and vibration to the user. Also, the supporting material would preferably be substantially opaque to light transmission, and the insulation or insulating material would be covered with a light absorbing material such as a tan or pink cotton sheet.

The acoustic vibrations produced by each of the transducers 304 may be directed upward through a mat 306 towards either the right side or left side of a user. Typically such vibrations will include some in the range of 50 Hz, among others. The mat 306 may be of any porous material which allows the sound and response vibrations to reach the user. Examples of some types of material that the mat may be composed of include, but are not limited to, polyethylene foam, sponge, cotton, and other foam rubbers and plastics, etc. The mat 306 may also have a covering that does not substantially attenuate the sound and response vibrations. In one embodiment of the present invention the mat 306 consists of four-inch thick open cell polyurethane foam compressible to a minimum of one-half inch thickness, sized to approximately match the inside length and width of the device shown in FIG. 1. A preferred covering for the mat 306 is a pink or tan cotton sheet. The mat 306 provides a cushion on which the user may lay, preferably on their back, with the midline of the body of the user substantially between the right and left transducers.

The light source 108 may be located in a position that corresponds to a level above the eyes of a typical user reclining upon support structure 208 of the enclosure 106 with the spine more or less aligned with said longitudinal centerline 308. Nevertheless, in some cases the user may be positioned so that his or her feet are under the light source and his or her head is at the opposite end of the enclosure from the light source.

The enclosure 106 may also have a temperature moderation and/or ventilation device attached at a vent 302. Such temperature moderation and/or ventilation devices include, but are not limited to, for example, a fan, a heater and an air conditioner. A ventilation feature is useful in view of the detoxing that often occurs in the employment of the present invention, and is included in one embodiment of this invention in the form of a fan and ductwork and designed to quietly exhaust any odors from the device. The vent 302 may be inserted in an end wall 206 or in other location that can accommodate a fan as a temperature moderation and/or ventilation device. Such devices may be mounted or equipped with light baffles to prevent unnecessary light from entering the substantially dark space.

Figure 4:
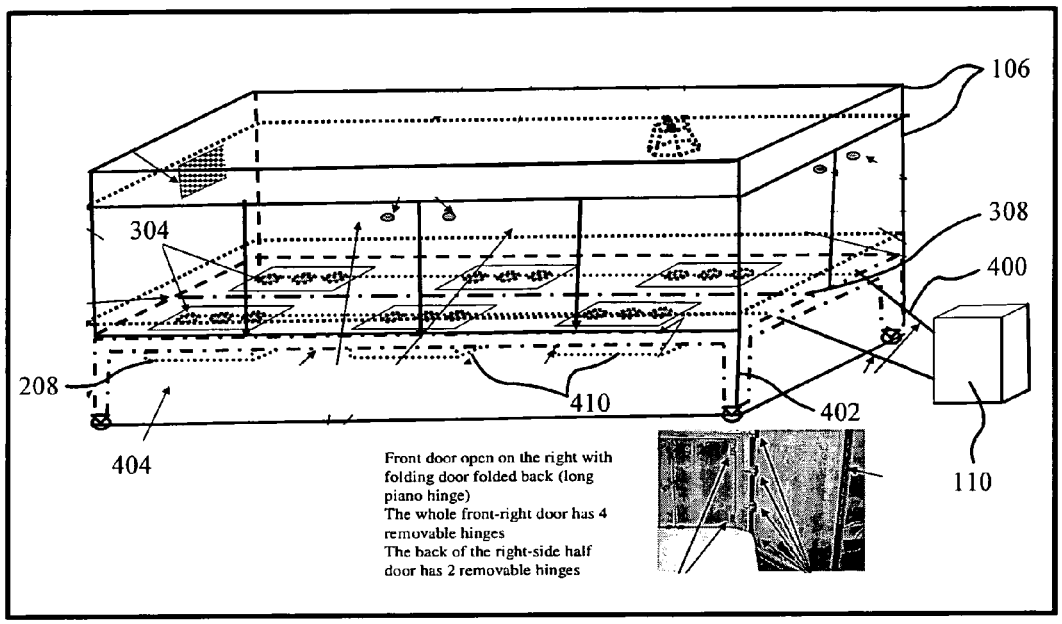
FIG. 4 is a perspective line drawing illustrating one embodiment a configuration for creating an individually balanceable environment of sound and light in accordance with the present invention.

FIG. 4 is a non-limiting perspective line drawing illustrating one embodiment of a configuration for creating an individually balanced environment of light and sound in accordance with the present invention. As depicted, the configuration comprises the enclosure module 106, the support structure 208, having a longitudinal center line 406, a signal generator 110, an output 400, a support member 402, a skirt 404, a plurality of sound transducers 304, and an attenuating barrier 410.

In the depicted embodiment the support member 402 stabilizes the support structure 208. Signals originating in the signal generator 110 may be transmitted via the output 400 to the transducers 304, which are positioned under areas of the support structure 208 corresponding to specific regions of the body of a user reclining on the support structure. The skirt 404 may help to contain the sound.

In various embodiments the support member 402 may be a single solid base or column, may be at least two supporting members or may be a plurality of four or more supporting members. In a further embodiment the support member may be mounted on movable wheels. The skirt 404, as well as other structural elements of the enclosure 106 may be constructed of a variety of materials including three-quarter inch thick particle board everywhere surfaced with one-thirty secondth of an inch thick formica attached thereto on those particular structural components of the device.

The signal generator 110 may have outputs 400 that are connected to the transducers 304 and may include either an internal or external amplifier to actuate the transducers. The signal generator 408 may be placed anywhere, including, for example on the top 210 of the enclosure 106 and a covering unit may be made to cover the signal generator 110.

At least two transducers 304 may be arranged on opposite sides of the longitudinal centerline 308. The longitudinal centerline 308, as defined for the purposes of this invention, corresponds to the right and left sides of a user in a reclined position within the enclosure, which may or may not correspond to the exact centerline of support. The transducers 304 corresponding to the right side of the user are also known as the right transducers 304A and the transducers 304 corresponding to the left side of the user are also known as the left transducers 304B.

The attenuating barrier 410 may be located along the longitudinal centerline of the support structure 208, separating the speakers positioned to the right and to the left of the center and directing the sound specifically to the right or left side (region) of the user. Attenuating barriers 410 may also be located between sets of speakers in such a way as to localize the delivery of sound to a particular segment of the right or left side of the user.

Controls for the signal generator and the actuating switches may be accessible to the user or may be controlled outside the substantially dark space 45. Preferably, the right transducer, or transducers 304A, and the left transducer, or transducers 304B, may be proportionally controlled, providing yet one more adjustment which may be useful in achieving an individually balanced environment. An example of proportional control is the ability to balance or imbalance inputs between the right transducer, or transducers 304A, and the left transducer or transducers 304B. More preferably, the right transducer, or transducers 304A, as a set, and the left transducer, or transducers 304B, as a set, may be independently controlled using separate controls. Most preferably, each transducer 304 may be independently controlled using a separate control. In another embodiment the light or lights may be selectively energized for duration and light intensity by an actuating switch.

Figure 5:
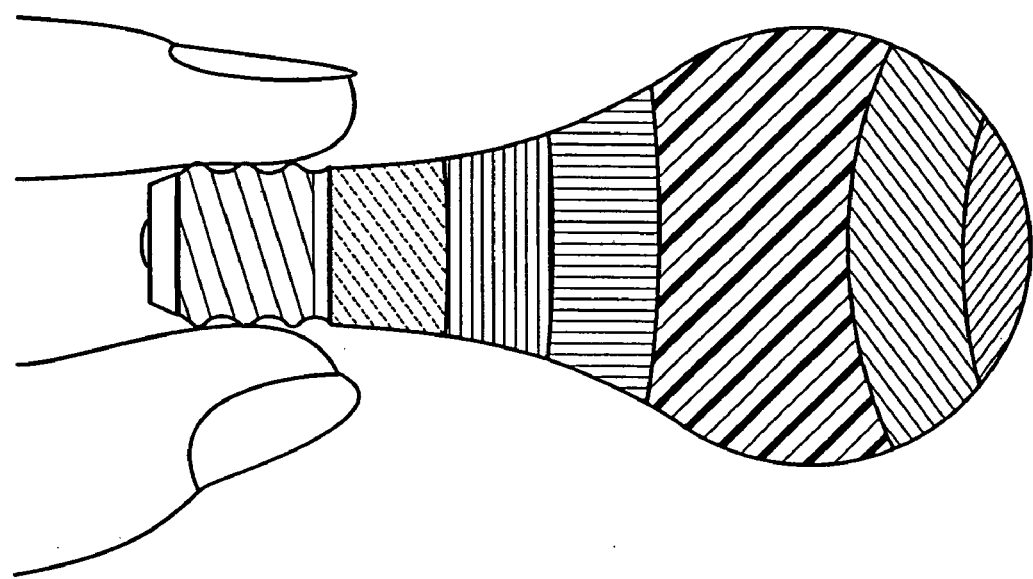
FIG. 5 is a photograph of a light source in accordance with the present invention.

FIG. 5 is a non-limiting photograph of a light source in accordance with the present invention. An incandescent bulb is depicted, but the light source may alternatively comprise a fluorescent light, a display terminal, simulated sunlight, a plasma screen, light emitting diodes, spectral arrays, other light source, and combinations thereof.

The light source may be configured to deliver light to the user with a wavelength in the range from about 400 nanometers to about 800 nanometers. In a one embodiment of the invention, the light source consists of a 40-watt incandescent light bulb manufactured by Special F/X Lighting, Inc., Hurricane, Utah and known as "The Amazing Rainbow Light" and designated A-19. Such a light bulb has spectral color bands applied to the surface of the bulb perpendicular to its axis of symmetry, as shown in FIG. 4. The light source 100 may be a white light source to simulate sunlight, provided that it is somehow separated into spectral colors using coatings, a prism or other means. Alternatively, the light source or sources may produce a spectral range of colored light by using a combination of individually colored lights or by using colored filters.

Separation of spectral colors in the light source(s) utilized appears to be important to cueing the physiological responses described herein as the basis upon which adjustments are made to the sound and light environment so as to achieve balance with respect to the individual. The balance which is achieved appears to have the effect of correcting any imbalance in the sympathetic and parasympathetic elements of the autonomic nervous system of the individual, as demonstrable by before and after data taken on the individual using an ANSAR ANX 3.0 Heart Rate Variability monitor.

Figure 6:
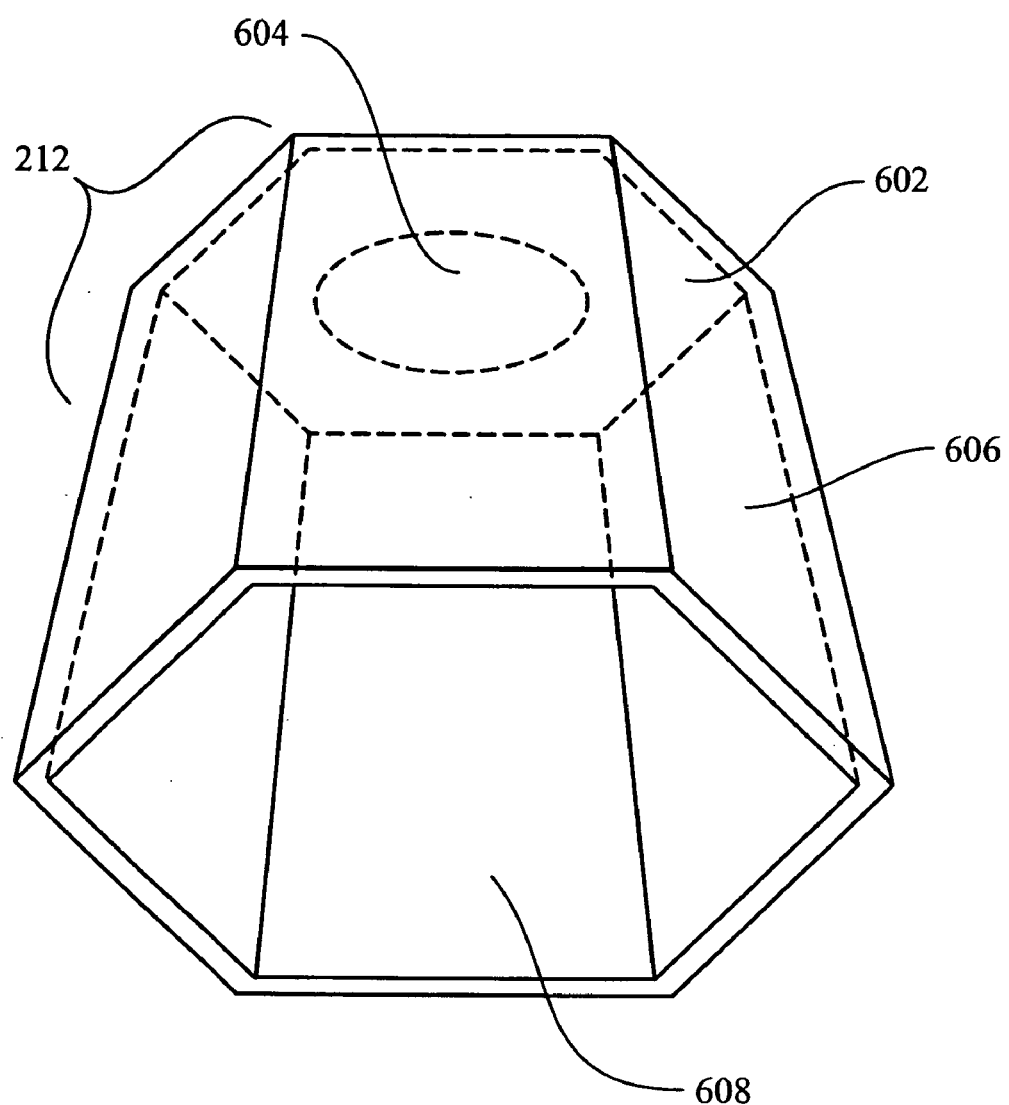
FIG. 6 is a perspective line drawing of deflective frame which may be used in an embodiment of the present invention.

FIG. 6 is a non-limiting perspective line drawing of an embodiment of the one or more reflective surfaces that may be positions around the light source. In the depicted embodiment the reflective surfaces comprise a reflective frame 212 which may be used in an embodiment of the present invention. The reflective surfaces direct the light toward distinct portions of the user's body. As depicted, the reflective frame 212 comprises a top 602, a hole 604 to admit the light source 212, angled sides 606, and an open end 608.

In one embodiment of the invention, the six-sided mirrored reflector 212 is constructed as shown in FIG. 6. The reflector may be made, for example, out of one-quarter inch thick glass plate, mirrored either on the second or the first surface, such as by aluminum evaporation. Alternatively, for example, the reflector could be made out of polished metal, such as polished aluminum, optically clear-coated to prevent corrosion.

The depicted dimensions of the reflector 212 were selected based upon sizing the reflector to be particularly effective with eye spacings typical of the average human being. If beings with much smaller or much larger eye spacings were being processed in the device, appropriately smaller or larger reflector dimensions would be preferable.

The light created within the enclosure is generated by the light bulb shown in FIG. 5 and reflector assembly shown in FIG. 6. The light is activated by a Crendenzo Lamp Dimmer Slider, Model #TT800. The Credenzo Lamp Dimmer Slider assembly has ten (10) equidistant settings identified that have been added to it by marking on it, which, when used in conjunction with the light bulb shown in FIG. 4, generates the output (i.e., electrical input to the bulb) data shown in Table 2.

Particular power settings for light inputs are shown in Table 2. For example, if the first set of light and sound frequencies and intensities (e.g., amplitudes or volumes) elicits a particular response or combination of responses in an individual, then a gradual transition to a second set of light and/or sound frequencies may occur resulting in the same individual showing another similar physiologic response or combination of responses in response to the second set or range of light and/or sound frequencies.

TABLE 2

| Slider Setting | Voltage | Amps |
|---|---|---|
| Off | 0 | 0.00 |
| Low—Low | 9 | 0.08 |
| Med–Low | 17 | 0.11 |
| High–Low | 24 | 0.12 |
| Low–Med | 30 | 0.14 |
| Med—Med | 38 | 0.15 |
| High–Med | 44 | 0.17 |
| Low–High | 58 | 0.20 |
| Med–High | 80 | 0.23 |
| High—High | 116 | 0.30 |

Figure 7A:
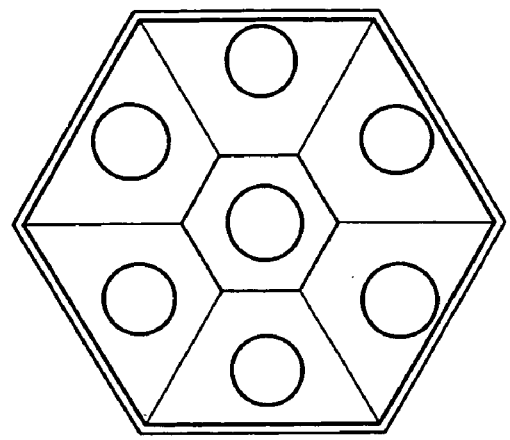
FIGS. 7a, 7b and 7c show photographs of light patterns which result at a series of different intensities when the light source is activated in the reflective frame.
Figure 7B:
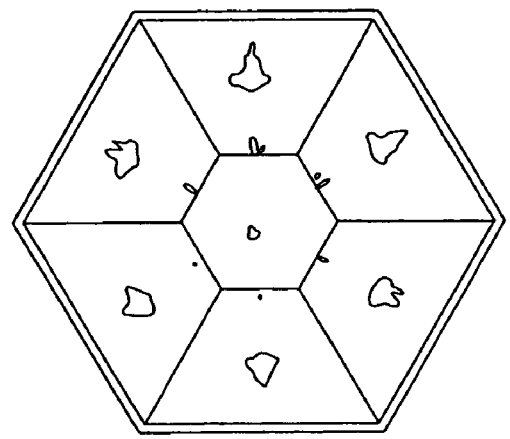
Figure 7C:
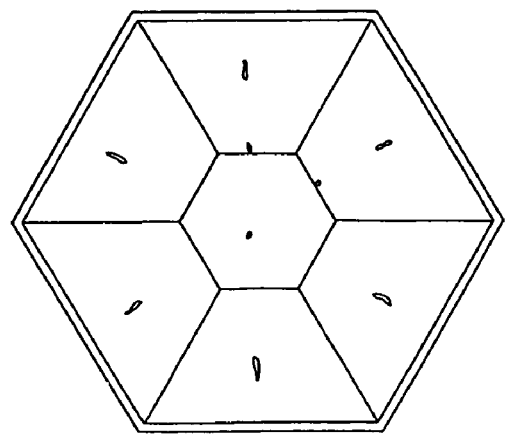

FIGS. 7a, 7b and 7c show non-limiting photographs of light patterns which result at a series of different intensities when the light source is activated in the reflective frame 212. FIG. 7a depicts the view that a user lying under the reflector would see with the Dimmer Slider on a High-High setting. FIG. 7b depicts the view that a user would see with the Dimmer Slider setting on medium. FIG. 9c depicts the view with the Dimmer Slider set on Low-Low.

Figure 8:
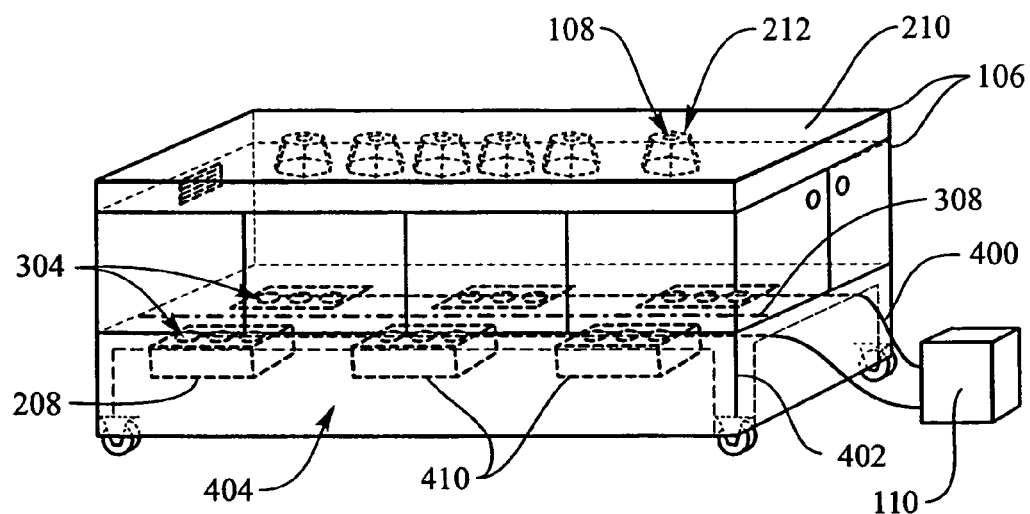
FIG. 8 is a perspective line drawing of an arrangement of lights that may be used in an embodiment in accordance with the present invention.

FIG. 8 is a non-limiting perspective line drawing illustrating one embodiment including multiple light sources 108 for creating an individually balanced environment of light and sound according to the present invention. In the depicted embodiment the six light sources 108 attached to the top 210 of the enclosure 106. The lights may each be enclosed in a six-sided reflective frame 212.

The light source or sources 108 produce light that is visible to the user's eyes and accessible to a lesser extent to the user's body, including, but not limited to, colors in the range of red, orange, yellow, violet, blue and green. The wavelengths of the light utilized are generally between 400 nanometers and 800 nanometers. The light source, or light sources, are coupled to the otherwise substantially dark space by placing the light source, or light sources, anywhere within the substantially dark space or the light may be transmitted by transmitting light into the substantially dark space by some method, such as, for example, fiber optics. The light source, or sources 108 may be mounted in the top 210 of the enclosure 106 so that light reaches the otherwise substantially dark space.

The light sources may be mounted above the user in a position normally anticipated to be directly above the eyes of the user when the user is in a reclining position within the light and sound environment. Alternatively, the light sources may be mounted along the extent of the longitudinal center of the top 210, as shown, or in other configurations. Further, the light source or light sources 108 may be controlled individually or in groups by actuating switches. The actuating switch may vary the intensity and/or duration of the variably energized light or light sources. In a further embodiment, each light source 108 has a separate actuating switch for varying the light source intensity.

Figure 9:
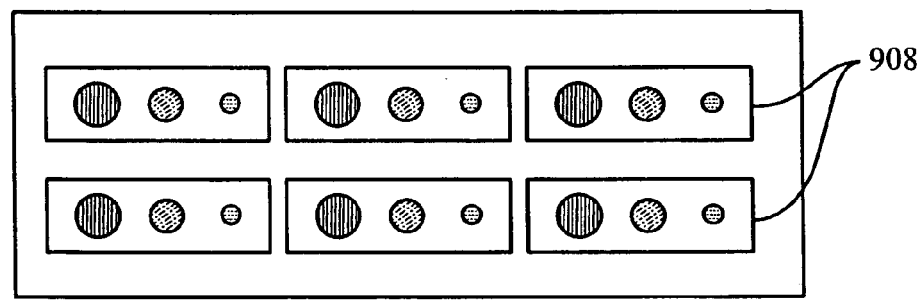
FIG. 9 is a top view of speaker locations in the support structure of one embodiment of the invention.

FIG. 9 is a non-limiting schematic of the arrangement of transducers (speakers) that may be used in an embodiment in accordance with the present invention. As depicted, the arrangement comprises a large transducer 902, a medium transducer 904, a small transducer 906, and a transducer set 908. Each transducer emits acoustic vibrations about the range of human auditory response. Light and sound vibrations can be defined by either the frequency or wavelength. In one embodiment the sound frequency range produced by the transducers is from about 10 Hz to about 25,000 Hz, and more specifically sound frequency produced may be from about 30 Hz to about 20,000 Hz. The transducers are also known as speakers. For example, individual speakers may be full range speakers or may produce frequencies of a limited range. The transducers may be electromechanical in nature. Limited range speakers are sometimes referred to as sub-woofers, woofers, mid-range and tweeters. In the depicted embodiment, the speakers (transducers) used were as follows:

TABLE 3

SPEAKERS

| Small Speakers 20t: (Tweeter) | Panasonic CJ-DC101 Impedence 0.4 Norm 20 - Peak SBASS4 - 600 Hz |
|---|---|
| Medium size speakers 20mr: (Mid-range) | MTX6522 Coaxial 75 watt peak power SBASS2 - 300 Hz |
| Large 8" speakers 20w: (Woofer) | Rockford 1.5 voice coil fosgate Punch 200 W max 4 ohms |

In the depicted embodiment the transducers 304 (i.e., comprising individual sets 908 of three (3) speakers, each set comprising one small speaker 20t (tweeter) 906, one medium size speaker 20mr (mid-range) 904 and one large speaker 20w (woofer) 902, may be located on the opposite sides of the longitudinal centerline 308 and may be separated by an attenuating barrier 410 placed between the transducers. The transducers 304 may be placed in groups of two or three or can be placed individually. At least one attenuating barrier 410 may be provided to reduce transmission of acoustical waves between the transducers 304 on opposite sides of the longitudinal centerline 308. Attenuating barriers 410 may also be placed between groups of or between individual transducers 304 on the same side. In a further embodiment an attenuating housing may be formed by fully enclosing the transducers 304, either in groups or individually.

In the depicted embodiment eighteen transducers 304 are grouped in six sets 908 of three attached to the bottom side of the support structure 208. The sets 908 of three transducers may be separated by attenuating barriers 410 which may form attenuating housings. The transducers 304 may be placed either above, below or mounted within the support structure 208. The transducers 304 may be attached to the support structure 208. The transducers 304 may be either attached to the top side, the bottom side, or set within the body of the enclosure 106.

If the transducers 304 are attached to the bottom of the support structure 208, then an acoustical transmitter should be used if the support does not substantially transmit the acoustic vibrations. Such an acoustical transmitter may be, for example, a plurality of holes in the support, a single opening in the support, or some frequency transmitting material in the support corresponding to the location of the transducers.

One example of the acoustical transmitter 26 may be an opening or holes that correspond to the removal of material in any shape and extending from the bottom side 208 of the support that allows for the transmission of the acoustic vibrations. For example the openings or holes may remove material in the shapes of cubes, parallelepipeds, spheres, pyramids, cones, cylinders, etc. A second type of acoustical transmitter may be a frequency transmitting material that may replace the opening or holes to allow for the transmission of the acoustic vibrations.

The sound created within the enclosure is generated by the transducers 304 which are actuated by the components shown in Table 4. While the sound produced directly by the transducers is typically 30 Hz and higher in frequencies, preliminary measurements indicate that lower frequency response vibrations are simultaneously created within the device in response to sound from the transducers by virtue of the design of the device of the present invention. For example, a thirty second segment of track 6 from Erin Jacobsen's album, "Feather on the Breath of God", was measured and found to contain no frequencies lower than 40 Hz, yet at the same time as transducers introduced this music into the device several frequencies less than 10 Hz were detected to be present within the device. Typically in operation sound frequencies in the range of 3 or 4 Hz appear to be created within the device by the introduction of musical tracks ranging from 30 to 20,000 Hz.

Figure 10:
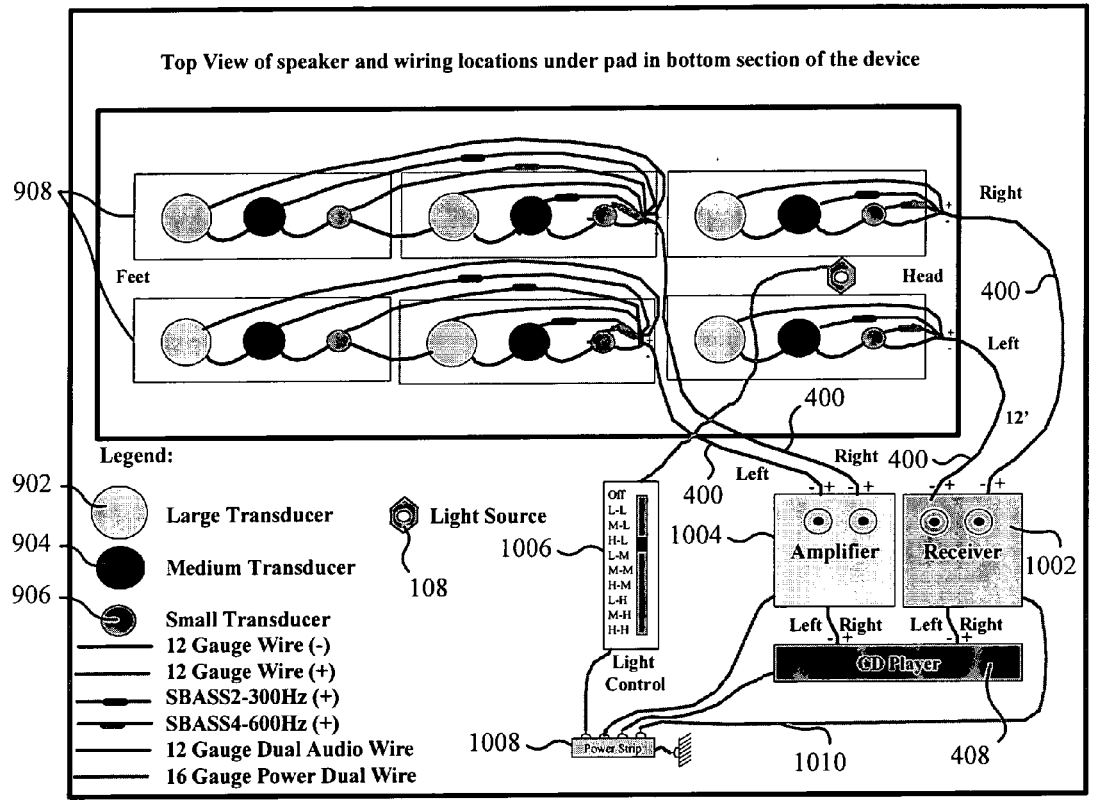
FIG. 10 is a wiring diagram showing the activation module for the transducers and light source of the embodiment.

FIG. 10 is a non-limiting wiring diagram showing on embodiment of the activation module 1000 for the transducers 20 and light source 100 of the embodiment. As depicted the activation module 1000 comprises the light source 108, large transducer 902, medium transducer 904, small transducer 906, transducer set 908, signal generator 408, receiver 1002, amplifier 1004, throughput 400, light control 1006, power strip 1008, and power cords 1010. Table 4 sets for the specifications for the depicted embodiment.

TABLE 4

1. Optimus SSM-1200 Stereo Sound Mixer with 7 band equalizer, manufactured by Radio Shack.

Input Impedance:

MIC 1, 2 (XLR Jack) - 0.5 mV 600 ohms (Low)
MIC 2 (Phone Jack) - 1 mV 600 Ohms (Low)
MIC 1, 2 (Phone Jack - 2.5 mV 10 kOhms (High)
CD/Line (CD 1, CH 2, CH 3, CH 4) - 120 mV 27 kOhms
PHONO (CH 1, CH 2, CH 3, CH 4) - 2 mV 50 kOhms
Output Level:

Recorder Out/Main Out - 0.775 V (0 dB)/1.5 V (6 dB)
Frequency Response - 20 Hz–20 kHz +/−1 dB
Distortion:

MIC - <0.5%
CD/Line - <0.05%
Phono - <0.08%
S/N Ratio:

MIC - 50 dB
CD/Line - 65 dB
Phono - 60 dB
Equalizer:

Control Frequency - 60 Hz, 150 Hz, 400 Hz, 1 kHz, 2.4 Khz, 6 kHz, 6 kHz, 15 kHz
Booster/Cut Range - +/−12 dB at Center
Talkover Attenuation - −12 dB TABLE 4-continued Echo - BBD System
Delay Time - 30 mS–200 mS with Echo
Power Source - AC 120 V/60 Hz
    2. Optimus MPA-250 Stereo Public Address Amplifier, manufactured
        by Radio Shack. Input Impedance: ~20 kOhms Continuous Output Power:
Stereo at 1 kHz - 125 Watts × 2 (8 Ohms)
Stereo at 1 kHz - 175 Watts × 2 (4 Ohms)
Bridged at 20 Hz to 20 kHz - 250 Watts (8 Ohms)
Bridged at 1 kHz: ~350 Watts (8 Ohms)
Total Harmonic Distortion: 0.1% at 80 Watts
Frequency Response (10 Hz–50 kHz): +/−3 dB
Input Sensitivity: 0.775 V
Signal-to-Noise Ratio: 90 dB (A-weighted)
Speaker Impedance:  A, B (4–16 Ohms)
                       A + B (8–16 Ohms)
                       Bridged (8–16 Ohms)
Power Requirement:  120 VAC. 60 Hz
    3. RCA Professional Stereo Receiver - Model #STAV 3880.

Continuous Power Output Rating

Front - 100 W per channel (1 kHz, 0.8%. 8 Ω)
Center - 100 W (1 kHz, 0.8%. 8 Ω)
Surround - 100 W per channel (1 kHz, 0.8%. 8 Ω)
Input (Sensitivity/Impedance) - 200 mV/47 k Ω
Frequency Response: ~5 Hz to 100,000 Hz dB
Output (Level/Impedance: ~200 mV/2.2 k Ω
Tone Control
Bass - +/−6 dB (100 Hz)
Treble - +/−6 dB (10 kHz)
Loudness - +/−9 dB/+9 dB (100 HZ/10 kHz)
Signal-to-Noise Ratio - 96 dB
Signal-to-Noise Ratio [E1A] at 1 W (1 kHz): ~79 dB
       4. Optimus CD-7200/7250 Compact Disc Automatic
       Changer - Model #CD7250, manufactured by Radio Shack.

Audio

Frequency Response: ~2 Hz to 20 kHz
Dynamic Range: ~95 dB or More (EIAJ)
Signal-to-Noise Ratio: ~98 dB or More (EIAJ)
Harmonic Distortion: ~0.005% or Less (EIAJ)
Wow and Flutter: ~Limit of Measurement (+/−0.001% or Less (EIAJ)
General Disc Diameter: ~5-Inch (12 cm)
Power Requirements - 120 V AC, 60 Hz
Power Consumption - 10 Watts All of the above components and the transducers 20 were connected together as shown in FIG. 10.

Figure 11:
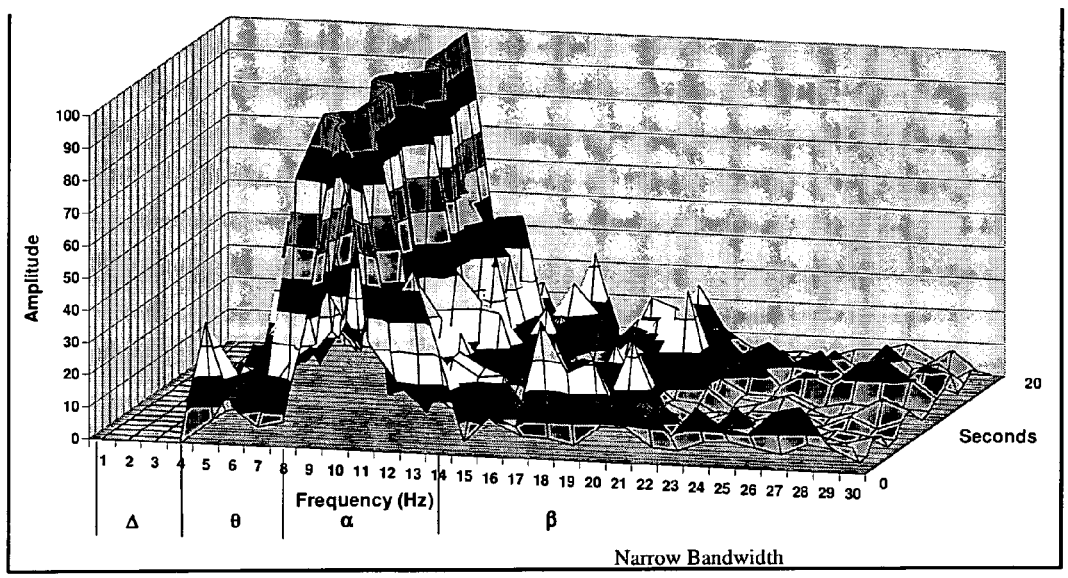
FIG. 11 depicts an EEG pattern for a human male subject prior to exposure to the balanced environment of sound and light of the present invention.

FIG. 11 depicts an EEG pattern for a human male subject prior to exposure to the balanced environment of sound and light of the present invention. The depicted case concerns a human male subject sixty-four years of age. FIG. 11 shows an awake and fully conscious state of this subject before exposure to the balanced environment of sound and light of the present invention, as measured by electroencephalograph (EEG). (Numerous EEGs of this same subject taken in awake and fully conscious states before such exposure showed the FIG. 11 EEG to be typical for such conditions for this subject).

Figure 12:
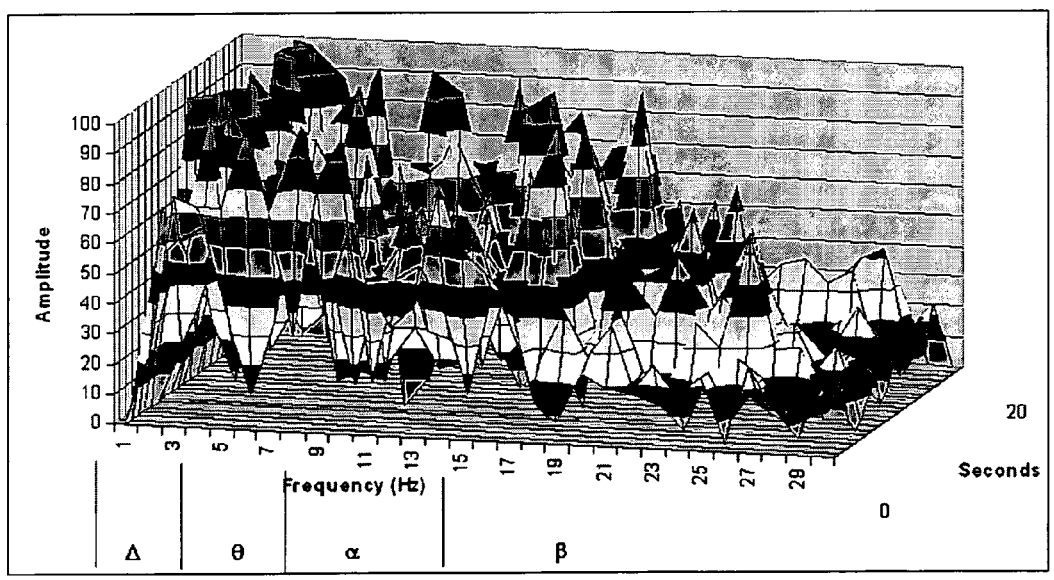
FIG. 12 depicts an EEG pattern for the same male subject as in FIG. 10 after 34 one-hour exposures to the balanced environment of sound and light of the present invention.

FIG. 12 depicts an EEG pattern for the same male subject as in FIG. 11 after 34 one-hour exposures to the balanced environment of sound and light of the present invention. The depicted EEG pattern was taken during an awake and fully conscious state of the same individual after thirty-four separate one hour exposures to the balanced environment of sound and light of the present invention, also as measured by EEG, and believed also to be typical of his awake and fully conscious brainwave state following such exposures. Of particular note in FIG. 12 is the ongoing presence with the individual of low frequency brainwave activity normally associated with elevated consciousness states. This individual has reported progressive healing improvement in medically-diagnosed conditions of diabetes and diabetic neuropathy during the period of a year over which the thirty-four exposures have occurred.

Figure 13:
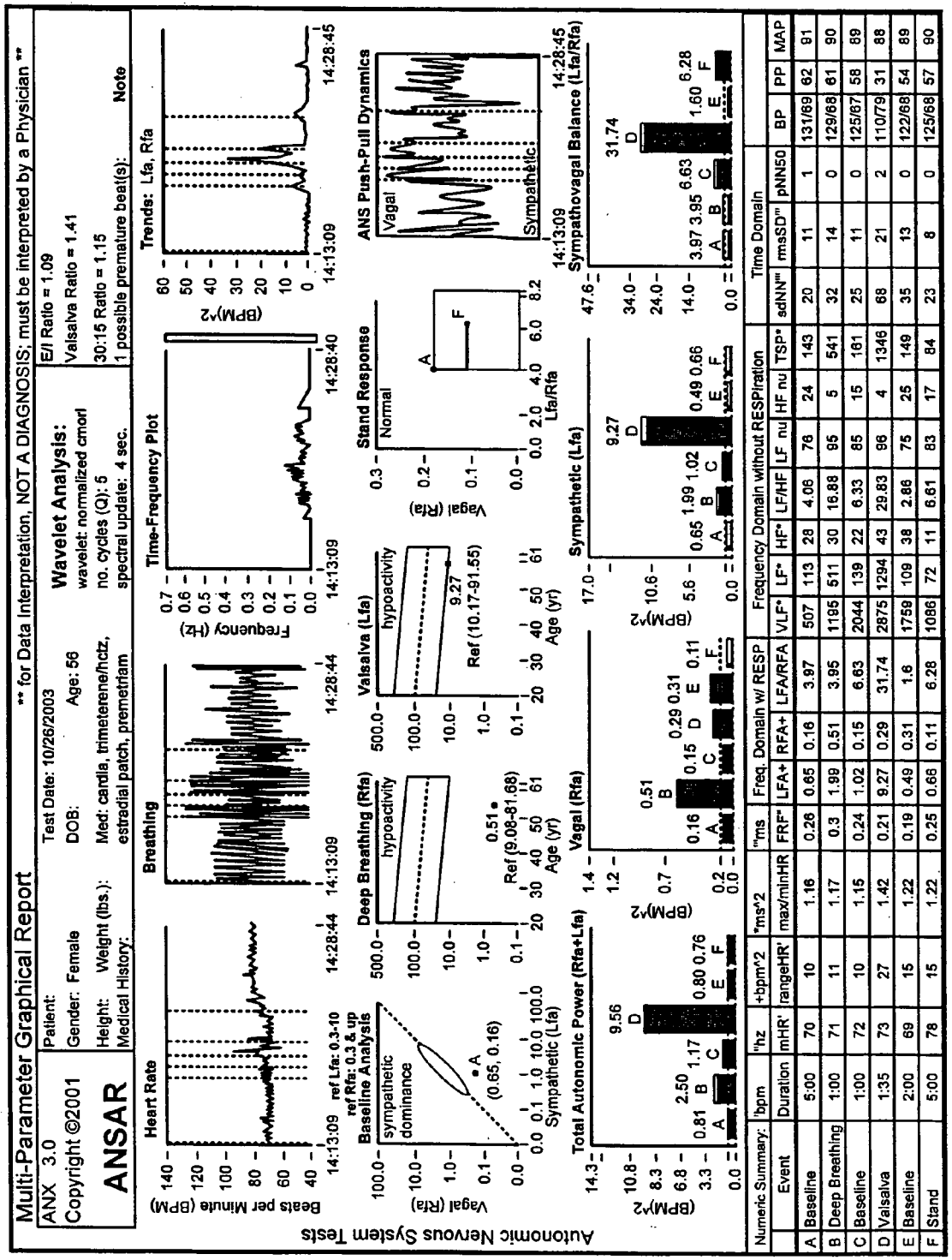
FIG. 13 depicts an HRV monitor report for a human female subject prior to exposure to the balanced environment of sound and light of the present invention.

FIG. 13 depicts an HRV monitor report for a human female subject prior to exposure to the balanced environment of sound and light of the present invention. FIG. 13 is the multiparameter graphic report output from an ANSAR ANX 3.0 HRV monitor for this subject immediately prior to any exposure to the balanced environment of sound and light of the present invention. The FIG. 13 report demonstrates major imbalance in the autonomic nervous system of the subject at that time, showing parasympathetic activity (per Deep Breathing Chart) of only 0.51 compared with sympathetic activity (per Valsalva chart) of 9.27, both of which are lower than expected respective activity for a healthy female reference subject of the same age (shown as shaded graphs on those respective charts). At that time the subject had been medically diagnosed for the previous five years as having hypertension (high blood pressure) and was being treated by drug therapy for the condition.

Figure 14:
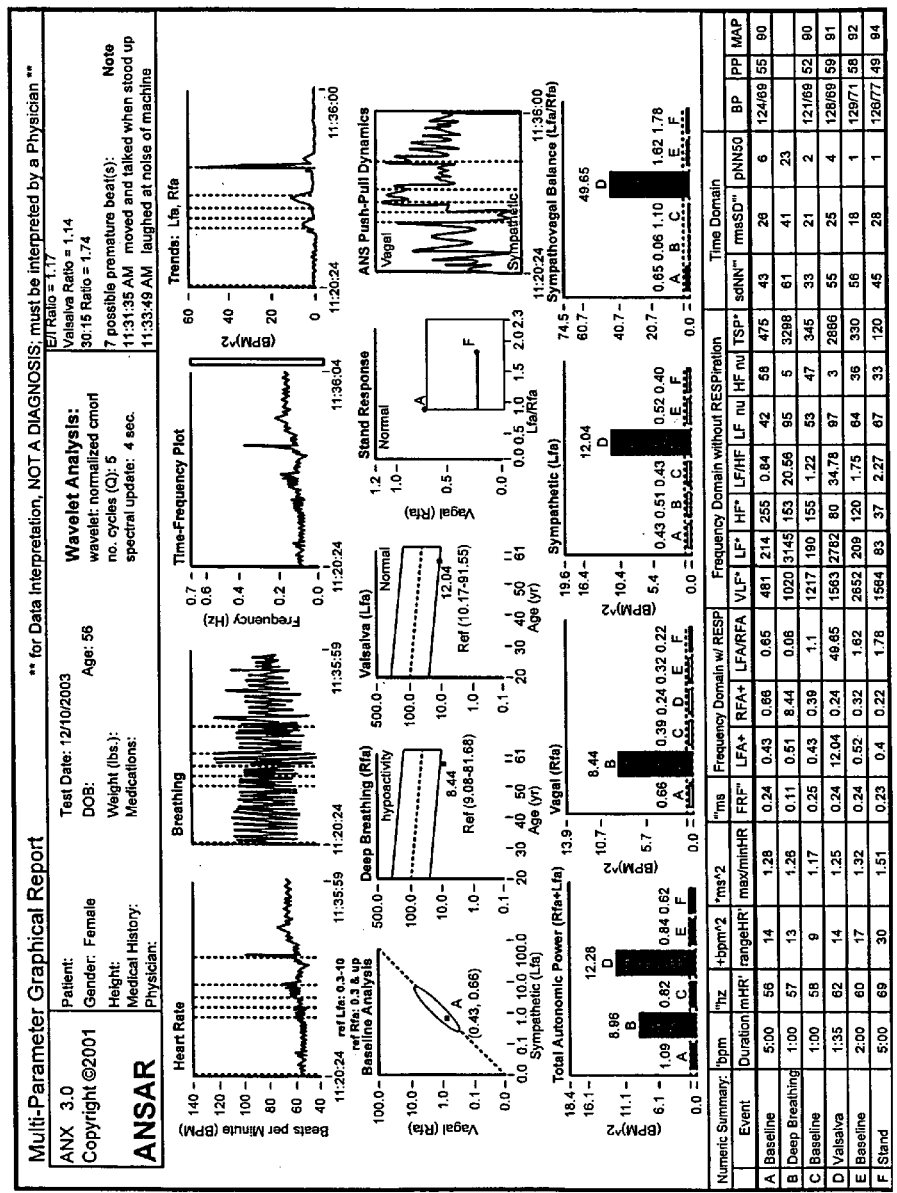
FIG. 14 depicts an HRV monitor report for the same female subject as in FIG. 12, after four one-hour exposures to the balanced environment of sound and light of the present invention.

FIG. 14 is an HRV monitor report for the same female subject as in FIG. 12, after four one-hour exposures to the balanced environment of sound and light of the present invention. FIG. 14 is a similar report from the HRV monitor for the same individual after eight one hour exposures to the balanced environment of sound and light of the present invention which occurred over a forty-three day interval. By the end of this period all medications had been discontinued as unnecessary for this subject. The FIG. 14 report shows parasympathetic activity increased to 8.44 and sympathetic activity increased to 12.04 on the respective charts. Both values evidence closer correspondence to expected activity for a healthy subject and a closer degree of balance of the autonomic nervous system following such exposure. The charts in FIGS. 13 and 14 show that after eight exposures the subject evidenced normal blood pressure (no hypertension) without medication as compared with somewhat higher BP values when previously on medication.

Figure 15:
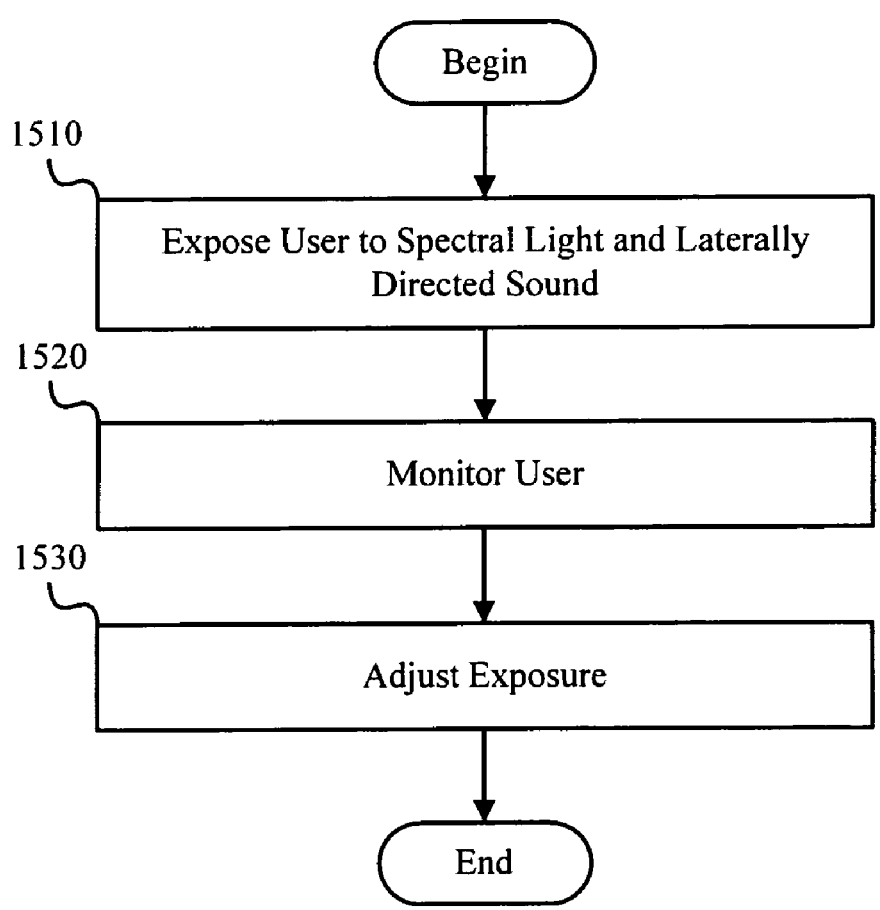
FIG. 15 is a schematic flow chart diagram illustrating one embodiment of a method for creating an individually balanceable environment of sound and light in accordance with the present invention.

FIG. 15 is a schematic flow chart diagram illustrating one embodiment of a method 1500 for an individually balanceable environment of sound and light in accordance with the present invention. As depicted, the method comprises the steps of exposing 1510 a user to spectral light and laterally directed sound, monitoring 1512 the user, and adjusting 1514 the manner of exposure sufficient to elicit a desired autonomic nervous response.

In a further embodiment of the invention, the method of creating an individually balanced environment of sound and light comprises the steps of: supporting a user on a support structure having a top side and including at least one right transducer arranged below the user's body corresponding to the user's right side and having at least one left transducer arranged below the user's body corresponding to the user's left side; transmitting acoustical vibrations from right transducers substantially to the right side of the user's body and simultaneously transmitting acoustical vibrations from the left transducers substantially to the left side of the user's body; providing an enclosure for forming a substantially dark space for the user; and coupling at least one variably energized light source to the otherwise substantially dark space for transmitting light to user.

Optionally, multiple light sources can be utilized, but they should be individually adjustable for intensity, and may be positioned along the longitudinal centerline of the enclosure, shining down on the user from the inside surface of the top of the enclosure. For example, six such light sources could be utilized, one located over the eyes of the user, one over the feet, and the other four distributed evenly between them, as shown in FIG. 8.

The sound inputs and light inputs are then individually adjusted to cause a very particular physiologic response (or combination of responses) from the user. These physiologic responses can be observed by an individual operator through a viewing slit or port to the outside of the device. The operator then adjusts, for example, levels of sound and/or light within certain predetermined ranges; or such response(s) can be observed by various types of monitoring devices such as low-light cameras, infrared cameras, electrodes connected to various portion of a user's body, etc., and thereafter controlling the sound and light inputs using a computer control (e.g., by software programming). For example, outputs of such monitoring devices can then be digitized to permit automatic adjustment or tuning of the light/sound environment based on the observed physiologic response(s).

The sound and/or light inputs are individually adjusted 1530 for each user by utilizing a series of procedures which occur in specific sequences, which procedures differ from individual-to-individual based on the observed physiologic responses from an individual when such individual is exposed to a first predetermined set of light and sound frequencies and intensities. For example, if the first set of light and sound frequencies and intensities (e.g., amplitudes or volumes) elicits a particular response or combination of responses in an individual, then a gradual transition to a second set of light and/or sound frequencies may occur resulting in the same individual showing another similar physiologic response or combination of responses in response to the second set or range of light and/or sound frequencies. These responses indicate the current state of the autonomic nervous system.

Some of the particular physiologic response(s) that are being sought and observed as a function of changing light and/or sound inputs are described with particularity immediately following.

Medical science has observed and classified a number of eye disorders which involves involuntary movement of the eyes generally as "nystagmus". Specifically, the term "nystagmus" is almost always associated with an involuntary oscillation of the eye(s). Types of "physiologic nystagmus" include end-point or eccentric-gaze nystagmus, vestibular nystagmus and optokinetic nystagmus. There are also particular infantile-onset nystagmus conditions known as congenital nystagmus and infantile nystagmus syndrome, which include: congenital periodic alternating nystagmus (related disorders include strabismus, albinism, optic nerve hypoplasia, anirdia, retinal dystrophies (including cone dystrophies)); latent/manifest latent nystagmus (fusional maldevelopment nystagmus syndrome); and spasmus nutans (spasmus nutans snydrome).

Further, there are also many known "acquired nystagmus" conditions including: see-saw nystagmus; periodic alternating nystagmus; downbeat nystagmus; upbeat nystagmus; gaze-enhanced nystagmus; vestibular nystagmus; etc.

Detailed reference is made to the various nystagmus conditions because various of these eye movements (and derivatives thereof) can occur in individuals exposed to the light and sound environments created by the present invention while they are within said environments. However, some eye movements not listed above also occur. These eye movements may actually be caused by eyeball movements which result in the movement of, for example, eyelashes, eyebrows, eyelids, etc. Moreover, it is possible that certain movements around the eyelash area may not involve direct movement of eyeballs at all, and may occur on their own (e.g., eyelashes and/or eyelids may move without the eyeballs actually moving).

The present invention teaches that by starting with known music at known intensities combined with known light sources at known intensities and then modifying the known light source to adjust it to another range of intensities followed by, or similar with, adjustments in intensity of known music, then physiologic responses involving, for example, the eye, eyelid, eyelash and/or eyebrow, can be observed. The specific physiologic responses sought by the aforementioned adjustments to light and sound sources is a quieting or stopping of involuntary movement in and around the eyes, with the eyeballs ultimately pointing in a forward direction while they are substantially static. This indicates a balanced state of the autonomic nervous system. When this condition is achieved, the environment of sound and light of the present invention is individually balanced to the user.

It has been noted with the present invention that eye movements as described above are not random, in the sense that they provide specific clues as to physical or emotional disharmonies present with the individual. For example, an involuntary right eye movement response might involve the eye pointing down and to the left, indicating an affliction in the individual's lower left quadrant. (The eyes seem to correspond to issues with the opposing half of the body: for example, involuntary right eye movements appear to relate to issues with the left side of the body). Experience gained with such indicators correlating them with specific afflictions can be used in the present invention as a means of diagnosis, if desired.

In certain cases it may prove impossible to individually balance the environment of sound and light to the user when the user is reclining in the typical position wherein his or her eyes are beneath a solitary light source within the enclosure. This circumstance appears to occur with individuals of reversed polarity, such as is the case with certain individuals with hormonal problems. In such cases the environment of sound and light of the present invention can be balanced to the user if the user's orientation is reversed within the device in the first exposure session, such that his or her feet are beneath the solitary light source. In such case such user's feet will provide the physiological responses necessary to determine when balance has been achieved. When the environment is yet unbalanced, such user's feet will tend to be somewhat rigid and pointed directly upward, and the toes will tend to be curled. When the environment becomes balanced, their feet will tend to relax forward or to the sides, and the toes will relax as well. After a first session of being balanced in this reversed position, the environment will normally be able to be balanced thereafter with the user in the typical position wherein his or her eyes are beneath the light source.

The monitor 114 or controller 116 may communicate with the user through various access ports, or through mechanical or electronic methods. Other examples of mechanical and electrical methods of communication systems are also feasible, such as two-way intercoms, etc. The sound and/or light inputs are individually adjusted for each user by utilizing a series of procedures which occur in specific sequences, which procedures differ from individual-to-individual based on the observed physiologic responses from the individual when such individual is first exposed to a predetermined set of light and sound frequencies and intensities.

In certain cases the device of the present invention may be operated in a partially open condition, such as with a side access door partially or completely open. This usually occurs in response to fears such as claustrophobia on the part of certain users. An arm of the user may extend out of this opening, for example, in the case of an uneasy child wanting to hold the hand of a parent outside the device. While operating the device in this partially open condition is not optimal, the device remains effective enough to be worthwhile, and after some balancing is achieved the uneasiness on the part of the user usually subsides so that subsequent operation can revert to a fully closed, more effective condition.

The present invention may also employ a controller to control the signal generator or generators, one or more light sources, or both. The controller may be either a specifically designed device or a general purpose computer employing a software program to control delivery of the sound and light to the user. In another preferred embodiment of the present invention, the controller may control any combination of the lights or the right and left transducers.

Figure 16:
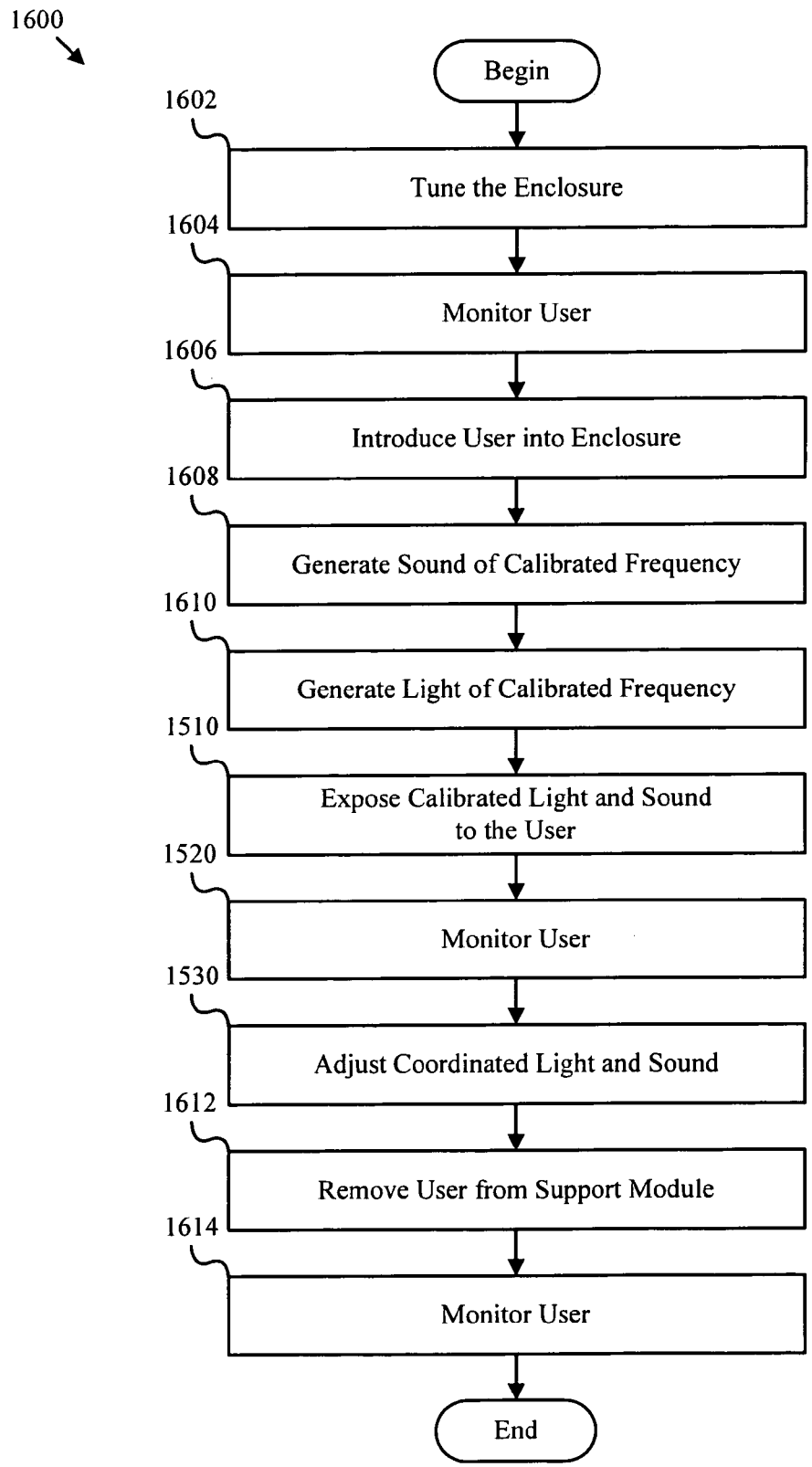
FIG. 16 is a schematic flow chart diagram illustrating a further embodiment of a method for creating an individually balanceable environment of sound and light in accordance with the present invention.

FIG. 16 is a schematic flow chart diagram illustrating a further embodiment of a method 1600 for an individually balanceable environment of light and sound in accordance with the present invention. As depicted, the method 1600 comprises the steps of tuning 1602 the enclosure, monitoring 1604 the user, introducing 1606 the user into the enclosure, generating 1608 sound of a calibrated frequency, generating 1610 light of a calibrated frequency, exposing 1510 a user to coordinated, calibrated light and sound; monitoring 1520 the user, adjusting 1530 the coordinated light and sound, removing 1612 the user from the enclosure; and monitoring 1614 the user.

In the depicted embodiment, a tuned enclosure is provided and an individual living being (e.g. a human, animal, bird, reptile, fish, etc.) is placed substantially therein. The individual may first have been monitored 1604 for autonomic nervous system activity and balance, using a technique such as HRV.

An individual is located within the enclosure such that the head of the individual is positioned substantially directly below the six-sided mirrored reflector 104. Certain combinations of sound and light are then applied within certain predetermined ranges therein, and adjusted based upon unique physiological responses of the living being.

The first musical selection, for example, Erin Jacobsen's "Feather on the Breath of God", is cued to play. The power setting for the sound may be set to be within a range of medium to low-high. The initial settings for the light begin between low-high and high-high, as defined in Table 2. The music album selection, "Feather on the Breath of God" begins to play on its first track and the operator begins to observe the behavior of the eyes, eyelids, eyebrows, and the area around the eyes of the user.

The first step after observing the behavior of the user's eye area is, typically, to adjust downward the power level settings on the slider device controlling the light source from the initial range down toward a second rage of medium-high, medium-low, as defined in Table 2. This process of reducing the intensity of light within the enclosure is accomplished over about one to two minutes. Typically, the only adjustment in this first stage is a light adjustment. The operator is at all times observing the user's eyes (and eye areas) in an attempt to quiet any observed movement. In this regard, the eyeballs themselves may show a slight movement, or vibration in response to the changing light intensity. This movement may be related to the nystagmus effects discussed above herein. The operator then pauses at the particular intensity where involuntary eye movement, a change in eye direction or, for example, a pointing of eyeballs, is noted. The operator may pause at this setting for a few moments (e.g., a few seconds to a minute or two minutes) and thereafter slightly increase the power setting and determine if the movement is attenuated and thereafter decrease the power setting to observe if movement is still present. The goal of this first step is to identify movement and to quiet the movement as much as possible.

If any movement persists, the operator may then proceed to adjust the sound inputs to the speakers or transducers from a position of low-high to medium down to a position of medium to medium-low. Once again, as the intensity of the sound is decreased, the operator is observing the eye-area response of the user to the changing intensity of sound. Once again, the goal is to quiet movement in and around the eye.

Once the operator has quieted additional movement, which movement may be the same or different than the initial movement observed, then the operator can continue to modify the intensity of the output of the light. In particular, the light setting is now, typically, at a medium-high to medium setting, as defined in Table 2; and the operator will, typically, then reduce the light intensity to a range of low-high to medium-low. Once again, as the light intensity is decreased the operator is constantly monitoring the behavior of the eye-area in an attempt to quiet any observed movement and obtain a forward-looking of the eyeballs (which can be observed through closed eyelids) as well as a balanced and static behavior of the eye-area. It is important to note that the individual within the device can be either asleep or awake, with eyes open or closed, with no important impact on the ability to create the balanced environment, since the physiological responses sought and interpreted are all involuntary responses oblivious to the state of awareness and conscious conduct of the individual.

Various slight modifications of sound and/or light intensities may now occur in an attempt to quiet all movement in and around the eye area. If proportional control of the transducers is present, this may also be adjusted by the operator to further attempt to quiet all movement in and around the eye. Once all movements in and/or around the eye area have been quieted, then the settings are maintained so that the total exposure time of the individual to the light and sounds within the enclosure will be from about 15 minutes to about two (2) hours, with the preferred amount of time being about 30 minutes to about one (1) hour. Moreover, once movement has stopped, the user shall be checked every 10–15 minutes to assure that no movement begins again.

In an initial session with a user, rebalancing is typically accomplished three or four times because of the occurrence of detoxing and destressing, which necessitates the rebalancing. Initial sessions with a user are normally not longer than about an hour because of the detoxing which may occur: it is important not to overload the ability of the individual's body to easily process the detoxing; an hour session does not provide undue physical stress in this regard. It is important for the user to drink at least a gallon of water per day during the first five to seven days following a session, as this relieves any potential side effect of the detoxing process on the individual.

In subsequent sessions with a user, balancing is typically only undertaken once or twice during the session, as less detoxing and distressing is usually occurring at that point.

Depending on the physical and emotional condition of the user, multiple sessions may be initially undertaken over a two to three day period. Aftereffects of healing progress typically occur over a three to four week period following a session with the device. If further sessions are deemed to be yet needed for additional improvement, they are typically undertaken around four weeks to a month or more apart.

Once a user has been subjected to the balanced environment of music and light for a sufficient amount of time (e.g., one-three hours total over, for example, separate one hour exposure times), significant physiological comparisons of the balance between the sympathetic and parasympathetic portions of the ANS can be made. For example, by using the ANSAR ANX 3.0 HRV device discussed above herein, improvements to ANS balance for an individual can be observed.

The schematic flow chart diagrams described above are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. The order in which a particular method occurs may or may not strictly adhere to the order of the corresponding steps shown.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An individually balanceable therapeutic light and sound system comprising:
   a signal generator;
   at least one selectively energized transducer;
   at least one selectively energized light source;
   a treatment monitor configured to monitor feedback received from a user exposed to light emitted by the light source and acoustical vibrations provided by the transducer;
   an enclosure module configured to substantially wholly enclose the user and configured to resonate to a specific musical tone; and
   one or more controllers for adjusting the light emitted by the light source and the acoustical vibrations provided by the transducers, based on input received from the treatment monitor, so as to elicit a desired autonomic nervous response in the user.

2. The system according to claim 1, wherein the at least one transducer is configured to selectively direct sound waves to one or more distinct regions of the user.

3. The system according to claim 1, further comprising at least one attenuating barrier located between first and second sets of transducers, the first and second sets of transducers positioned wholly on opposite sides of a longitudinal centerline beneath the user, the first set of transducers being located to allow the acoustical vibrations emitted by the first set of transducers to travel substantially directly through air from the first set of transducers to a first side of the user.

4. The system according to claim 1, further comprising at least one outside monitor configured to monitor a response of the user to the applied light and acoustical vibrations and the autonomic nervous system of the user.

5. The system according to claim 4, wherein the outside monitor utilizes a heart rate variation ["HRV"] technique.

6. The apparatus of claim 1, wherein the feedback comprises movement in and around the user's eyes.

7. The apparatus of claim 1, wherein the feedback comprises the position of the user's feet.

8. An apparatus for therapeutic light and sound, the apparatus comprising:
   a support structure comprising a longitudinal centerline and a top side for supporting a user having a right side and a left side;
   a pair of speakers arranged on the support structure underneath the user for transmitting acoustic vibrations selectively to a right side and a left side of the user;
   at least one attenuating barrier located between the pair of speakers arranged on opposite sides of the longitudinal centerline;
   at least one light source comprising visible light;
   one or more controllers configured to adjust acoustical vibrations produced by the speakers and intensity of the light source such that the acoustic vibrations and the light source are coordinated to therapeutically stimulate the user;
   an enclosure module configured to substantially wholly enclose the user and configured to resonate to a specific musical tone; and
   a monitor configured to monitor at least one of the user's autonomic nervous system and the user's response to the applied light and sound.

9. The apparatus of claim 8, wherein the enclosure module is configured to transmute applied acoustical vibrations to a lower frequency.

10. The apparatus of claim 8, wherein the enclosure module is configured to resonate in the range of a C flat minor tone and its harmonics.

11. The apparatus of claim 8, further comprising one or more reflective surfaces positioned around the light source in at least one of a separate surface configuration and a frame configuration.

12. A method for applying therapeutic light and sound, the method comprising:
   substantially wholly enclosing a user in an enclosure module, wherein the enclosure module is coupled to at least one light source that produces visible light and the enclosure module is configured to resonate to a specific musical tone;
   exposing the user to spectral light and laterally directed sound, the sound being emitted from beneath the user's body;
   monitoring the state of the user's autonomic nervous system; and
   eliciting a desired autonomic nervous response in the user in response, to adjusting the magnitude of exposure of light and sound.

13. The method according to claim 12, further comprising transmitting acoustical vibrations specifically to distinct areas of a user's body.

14. The method according to claim 12, further comprising calibrating a sound frequency for the directed sound to correspond to the resonance frequency of specific body tissues.

15. The method according to claim 14, further comprising controlling the sound generator and at least one selectively energized light source using a controller.

16. The method according to claim 12, further comprising monitoring at least one of the user's responses to the spectral light, sound, and the user's autonomic nervous system.

17. The method according to claim 16, further comprising adjusting at least one of the light and sound frequency in response to the monitoring feedback.

18. The method according to claim 16, wherein monitoring at least one of the user's responses comprises monitoring movement in and around the user's eyes.

19. The method according to claim 16, wherein monitoring at least one of the user's responses comprises monitoring the position of the user's feet.

20. The method of claim 12, further comprising causing the enclosure module to resonate to a C-flat minor chord.

21. The method of claim 12, further comprising transmuting acoustical vibrations to a lower frequency in the enclosure module.

* * * * *